(12) United States Patent
Rothberg et al.

(10) Patent No.: US 11,774,401 B2
(45) Date of Patent: Oct. 3, 2023

(54) CHEMICAL SENSOR ARRAY HAVING MULTIPLE SENSORS PER WELL

(71) Applicant: Life Technologies Corporation, Carlsbad, CA (US)

(72) Inventors: Jonathan M. Rothberg, Guilford, CT (US); Keith G Fife, Palo Alto, CA (US); Jordan Owens, Austin, TX (US); James Bustillo, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 18/045,106

(22) Filed: Oct. 7, 2022

(65) Prior Publication Data

US 2023/0125333 A1    Apr. 27, 2023

Related U.S. Application Data

(60) Continuation of application No. 17/070,142, filed on Oct. 14, 2020, now Pat. No. 11,499,938, which is a division of application No. 16/663,052, filed on Oct. 24, 2019, now Pat. No. 10,816,504, which is a division of application No. 14/293,247, filed on Jun. 2, 2014, now Pat. No. 10,458,942.

(60) Provisional application No. 61/833,375, filed on Jun. 10, 2013.

(51) Int. Cl.
*G01N 27/414* (2006.01)
*C12Q 1/6874* (2018.01)
*H01L 29/66* (2006.01)

(52) U.S. Cl.
CPC ....... *G01N 27/4145* (2013.01); *C12Q 1/6874* (2013.01); *G01N 27/414* (2013.01); *H01L 29/66825* (2013.01)

(58) Field of Classification Search
CPC ............. G01N 27/414; G01N 27/4145; G01N 27/4148; H01L 29/66825; C12G 1/6874
USPC ....................... 257/253, 23.08; 438/10; 506/2
See application file for complete search history.

(56) References Cited

U.S. PATENT DOCUMENTS

| | | | |
|---|---|---|---|
| 4,086,642 A | 4/1978 | Yoshida et al. | |
| 4,411,741 A | 10/1983 | Janata | |
| 4,437,969 A | 3/1984 | Covington et al. | |

(Continued)

FOREIGN PATENT DOCUMENTS

| | | |
|---|---|---|
| CN | 1582334 A | 2/2005 |
| CN | 101676714 A | 3/2010 |

(Continued)

OTHER PUBLICATIONS

Ahmadian A., et al., "Single-Nucleotide Polymorphism Analysis by Pyrosequencing," Analytical and Biochemistry, 2000, vol. 280, pp. 103-110.

(Continued)

*Primary Examiner* — Matthew E. Gordon

(57) ABSTRACT

In one embodiment, a device is described. The device includes a material defining a reaction region. The device also includes a plurality of chemically-sensitive field effect transistors have a common floating gate in communication with the reaction region. The device also includes a circuit to obtain respective output signals from the chemically-sensitive field effect transistors indicating an analyte within the reaction region.

20 Claims, 15 Drawing Sheets

(56) References Cited

U.S. PATENT DOCUMENTS

| | | |
|---|---|---|
| 4,438,354 A | 3/1984 | Haque et al. |
| 4,444,644 A | 4/1984 | Hiramoto et al. |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | V'd et al. |
| 4,701,253 A | 10/1987 | Ligtenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau et al. |
| 5,110,441 A | 5/1992 | Kinlen et al. |
| 5,113,870 A | 5/1992 | Rossenfeld |
| 5,126,759 A | 6/1992 | Small et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,262,568 B1 | 7/2001 | Komatsu et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges, III et al. |
| 7,084,641 B2 | 8/2006 | Brederlow et al. |
| 7,085,502 B2 | 8/2006 | Shushakov et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,092,757 B2 | 8/2006 | Larson et al. |
| 7,097,973 B1 | 8/2006 | Zenhausern |
| 7,105,300 B2 | 9/2006 | Parce et al. |

(56) References Cited

U.S. PATENT DOCUMENTS

| | | |
|---|---|---|
| 7,106,089 B2 | 9/2006 | Nakano et al. |
| 7,129,554 B2 | 10/2006 | Lieber et al. |
| 7,169,560 B2 | 1/2007 | Lapidus et al. |
| 7,173,445 B2 | 2/2007 | Fujii et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg et al. |
| 7,220,550 B2 | 5/2007 | Keen |
| 7,223,540 B2 | 5/2007 | Pourmand et al. |
| 7,226,734 B2 | 6/2007 | Chee et al. |
| 7,229,799 B2 | 6/2007 | Williams |
| 7,235,389 B2 | 6/2007 | Lim et al. |
| 7,238,323 B2 | 7/2007 | Knapp et al. |
| 7,239,188 B1 | 7/2007 | Xu et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,476,504 B2 | 1/2009 | Turner |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,590,211 B1 | 9/2009 | Burney |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee et al. |
| 7,612,369 B2 | 11/2009 | Stasiak |
| 7,612,817 B2 | 11/2009 | Tay |
| 7,614,135 B2 | 11/2009 | Santini, Jr. et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,824,900 B2 | 11/2010 | Iwadate et al. |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,072,188 B2 | 12/2011 | Yorinobu et al. |
| 8,114,591 B2 | 2/2012 | Toumazou et al. |
| 8,124,936 B1 | 2/2012 | Lagna |
| 8,133,698 B2 | 3/2012 | Silver |
| 8,138,496 B2 | 3/2012 | Li et al. |
| 8,154,480 B2 | 4/2012 | Shishido et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,383,896 B2 | 2/2013 | Floyd |
| 8,415,716 B2 | 4/2013 | Rothberg et al. |
| 8,421,437 B2 | 4/2013 | Levine |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,487,790 B2 | 7/2013 | Fife et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |

(56) References Cited

U.S. PATENT DOCUMENTS

| | | |
|---|---|---|
| 8,558,288 B2 | 10/2013 | Rothberg et al. |
| 8,575,664 B2 | 11/2013 | Rothberg et al. |
| 8,592,154 B2 | 11/2013 | Rearick |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rockenschaub et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,748,947 B2 | 6/2014 | Milgrew |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,776,573 B2 | 7/2014 | Rearick et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,823,380 B2 | 9/2014 | Levine et al. |
| 8,841,217 B1 | 9/2014 | Fife et al. |
| 8,847,637 B1 | 9/2014 | Guyton |
| 8,912,005 B1 | 12/2014 | Fife et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,164,070 B2 | 10/2015 | Fife |
| 9,201,041 B2 | 12/2015 | Dalton et al. |
| 9,270,264 B2 | 2/2016 | Jordan et al. |
| 9,389,199 B2 | 7/2016 | Cheng et al. |
| 9,618,475 B2 | 4/2017 | Rothberg et al. |
| 9,671,363 B2 | 6/2017 | Fife et al. |
| 2002/0012933 A1 | 1/2002 | Rothberg et al. |
| 2002/0042388 A1 | 4/2002 | Cooper et al. |
| 2002/0070791 A1 | 6/2002 | Dabral |
| 2002/0081714 A1 | 6/2002 | Jain et al. |
| 2002/0085136 A1 | 7/2002 | Moon et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0152994 A1 | 8/2003 | Woudenberg et al. |
| 2003/0155942 A1 | 8/2003 | Thewes |
| 2003/0175990 A1 | 9/2003 | Hayenga et al. |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0227296 A1 | 12/2003 | Lee |
| 2004/0002470 A1 | 1/2004 | Keith et al. |
| 2004/0023253 A1 | 2/2004 | Kunwar et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0093645 A1 | 5/2005 | Watanabe et al. |
| 2005/0106587 A1 | 5/2005 | Klapproth et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0239132 A1 | 10/2005 | Klapproth |
| 2005/0282224 A1 | 12/2005 | Fouillet et al. |
| 2006/0000772 A1 | 1/2006 | Sano et al. |
| 2006/0024711 A1 | 2/2006 | Lapidus et al. |
| 2006/0035400 A1 | 2/2006 | Wu et al. |
| 2006/0038601 A1 | 2/2006 | Giguere et al. |
| 2006/0057025 A1 | 3/2006 | Eversmann et al. |
| 2006/0057604 A1 | 3/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0266946 A1 | 11/2006 | Defrise et al. |
| 2006/0269927 A1 | 11/2006 | Lieber et al. |
| 2006/0289726 A1 | 12/2006 | Paulus et al. |
| 2007/0031291 A1 | 2/2007 | Piech et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0096216 A1 | 4/2008 | Quake |
| 2008/0111161 A1 | 5/2008 | Sorge et al. |
| 2008/0121946 A1 | 5/2008 | Youn et al. |
| 2008/0136933 A1 | 6/2008 | Dosluoglu et al. |
| 2008/0164917 A1 | 7/2008 | Floyd et al. |
| 2008/0178692 A1 | 7/2008 | Jung et al. |
| 2008/0185616 A1 | 8/2008 | Johnson et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0048124 A1 | 2/2009 | Leamon et al. |
| 2009/0062132 A1 | 3/2009 | Borner |
| 2009/0075383 A1 | 3/2009 | Buschmann et al. |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127689 A1 | 5/2009 | Ye et al. |
| 2009/0149607 A1 | 6/2009 | Karim et al. |

(56) References Cited

U.S. PATENT DOCUMENTS

| | | |
|---|---|---|
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0273386 A1 | 11/2009 | Korobeynikov et al. |
| 2009/0299138 A1 | 12/2009 | Mitsuhashi |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1* | 6/2010 | Rothberg ............ C12Q 1/6869 506/38 |
| 2010/0176463 A1 | 7/2010 | Koizumi et al. |
| 2010/0244106 A1 | 9/2010 | Parker et al. |
| 2010/0273166 A1 | 10/2010 | Garcia |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0236263 A1 | 9/2011 | Sawada et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001236 A1 | 1/2012 | Fife |
| 2012/0001237 A1 | 1/2012 | Fife et al. |
| 2012/0001615 A1 | 1/2012 | Levine |
| 2012/0001616 A1* | 1/2012 | Fife .................... G01N 27/4148 324/71.5 |
| 2012/0001646 A1 | 1/2012 | Bolander et al. |
| 2012/0013392 A1 | 1/2012 | Rothberg et al. |
| 2012/0034607 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0060587 A1 | 3/2012 | Babcock et al. |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0173159 A1 | 7/2012 | Davey et al. |
| 2012/0249192 A1 | 10/2012 | Matsushita |
| 2012/0261274 A1 | 10/2012 | Rearick et al. |
| 2012/0286771 A1 | 11/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329192 A1 | 12/2012 | Bustillo et al. |
| 2013/0001653 A1 | 1/2013 | Milgrew et al. |
| 2013/0009214 A1 | 1/2013 | Bustillo et al. |
| 2013/0027594 A1 | 1/2013 | Krymski |
| 2013/0056353 A1 | 3/2013 | Nemirovsky et al. |
| 2013/0105868 A1 | 5/2013 | Kalnitsky et al. |
| 2013/0135018 A1 | 5/2013 | Kuo et al. |
| 2013/0189790 A1 | 7/2013 | Li et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0273664 A1* | 10/2013 | Toumazou ......... G01N 27/4148 257/253 |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0075237 A1 | 3/2014 | Ware |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235463 A1 | 8/2014 | Rothberg et al. |
| 2014/0308752 A1 | 10/2014 | Chang et al. |
| 2014/0367748 A1 | 12/2014 | Dalton et al. |
| 2015/0097214 A1 | 4/2015 | Chen et al. |
| 2016/0178568 A1 | 6/2016 | Cheng et al. |
| 2017/0038334 A1 | 2/2017 | Barbee et al. |
| 2017/0059514 A1 | 3/2017 | Hoffman |
| 2017/0102356 A1 | 4/2017 | Lin et al. |

FOREIGN PATENT DOCUMENTS

| | | |
|---|---|---|
| DE | 4232532 A1 | 4/1994 |
| DE | 4430811 C1 | 9/1995 |
| DE | 102004044299 A1 | 3/2006 |
| DE | 102008012899 A1 | 9/2009 |
| EP | 1243925 A2 | 9/2002 |
| EP | 1371974 A1 | 12/2003 |
| EP | 1542009 A1 | 6/2005 |
| EP | 1669749 A1 | 6/2006 |
| EP | 1870703 A1 | 12/2007 |
| EP | 1975246 A1 | 10/2008 |
| JP | S5870155 A | 4/1983 |
| JP | S62237349 A | 10/1987 |
| JP | H02250331 A | 10/1990 |
| JP | H02310931 A | 12/1990 |
| JP | H0580115 A | 4/1993 |
| JP | H1078827 A | 3/1998 |
| JP | 2000055874 A | 2/2000 |
| JP | 2002221510 A | 8/2002 |
| JP | 2002272463 A | 9/2002 |
| JP | 2003279532 A | 10/2003 |
| JP | 2003322633 A | 11/2003 |
| JP | 2004500033 A | 1/2004 |
| JP | 2004343441 A | 12/2004 |
| JP | 2005515475 A | 5/2005 |
| JP | 2006138846 A | 6/2006 |
| JP | 2006284225 A | 10/2006 |
| JP | 2007512810 A | 5/2007 |
| JP | 2008215974 A | 9/2008 |
| TW | 200946904 A | 11/2009 |
| WO | WO-2004040291 A1 | 5/2004 |
| WO | WO-2004048962 A1 | 6/2004 |
| WO | WO-2005015156 A2 | 2/2005 |
| WO | WO-2005054431 A2 | 6/2005 |
| WO | WO-2005062049 A2 | 7/2005 |
| WO | WO-2005084367 A2 | 9/2005 |
| WO | WO-2005090961 A1 | 9/2005 |
| WO | WO-2006056226 A1 | 6/2006 |
| WO | WO-2007002204 A2 | 1/2007 |
| WO | WO-2008058282 A2 | 5/2008 |
| WO | WO-2008107014 A1 | 9/2008 |
| WO | WO-2009001917 A1 | 4/2009 |
| WO | WO-2010047804 A1 | 4/2010 |
| WO | WO-2010138186 A1 | 12/2010 |
| WO | WO-2012046137 A1 | 4/2012 |
| WO | WO-2012152308 A1 | 11/2012 |

OTHER PUBLICATIONS

Akiyama et al., "Ion-Sensitive Field-Effect Transistors with Inorganic Gate Oxide for pH Sensing", IEEE Transactions on Electron Devices, vol. 29, No. 12, 1982, pp. 1936-1941.

Bandettini et al., "Processing Strategies for Time-Course Data Sets in Functional MRI of the Human Brain," MRM, vol. 30, 1993, pp. 161-172.

Bandiera et al., "A fully electronic sensor for the measurement of cDNA hybridization kinetics", Biosensors & Bioelectronics, vol. 22, Nos. 9-10, Apr. 15, 2007, pp. 2108-2114.

Barbaro et al., "A Charge-Modulated FET for Detection of Biomolecular Processes: Conception, Modeling, and Simulation", IEEE

(56) References Cited

OTHER PUBLICATIONS

Transactions on Electron Devices, vol. 53, No. 1, 2006, pp. 158-166.
Barbaro et al., "A CMOS, Fully Integrated Sensor for Electronic Detection of DNA Hybridization", IEEE Electronic Device Letters, vol. 27, No. 7, 2006, pp. 595-597.
Barbaro M., et al., "Fully Electronic DNA Hybridization Detection by a Standard CMOS Biochip," Sensors and Actuators B: Chemical, 2006, vol. 118, pp. 41-46.
Bashford et al., "Automated bead-trapping apparatus and control system for singlemolecule DNA sequencing", Optics Express, vol. 16, No. 5, Mar. 3, 2008, pp. 3445-3455.
Baumann et al., "Microelectronic sensor system for microphysiological application on living cells", Sensors and Actuators B: Chemical, vol. 55, No. 1, Apr. 1999, pp. 77-89.
Bausells et al., "Ion-sensitive field-effect transistors fabricated in a commercial CMOS technology", Sensors and Actuators B: Chemical, vol. 57, Nos. 1-3, 1999, pp. 56-62.
Bergveld, "ISFET, Theory and Practice", IEEE Sensor Conference, Toronto, Oct. 2003, pp. 1-26.
Bergveld P., "Thirty years of ISFETOLOGY What happened in the past 30 years and what may happen in the next 30 years," Sensors and Actuators B: Chemical, Jan. 2003, vol. 88, No. 1, pp. 1-20.
Besselink et al., "ISFET Affinity Sensor", Chapter 12 in Methods in Biotechnology, Affinity Biosensors: Techniques and Protocols, vol. 7, 1998, pp. 173-185.
Bobrov et al., "Chemical sensitivity of an ISFET with Ta2O5 membrane in strong acid and alkaline solutions", Sensors and Actuators B: Chemical, vol. 3, No. 1, Jan. 1991, pp. 75-81.
Bockelmann et al., "Detecting DNA by field effect transistor arrays", Proceedings of the 2006 IFIP International Conference on Very Large Scale Integration, 2006, pp. 164-168.
Bousse et al., "A process for the combined fabrication of ion sensors and CMOS circuits", IEEE Electron Device Letters, vol. 9, No. 1, Jan. 1988, pp. 44-46.
Bousse et al., "Zeta potential measurements of Ta2O5 and SiO2 thin films" Journal of Colloid and Interface Science, vol. 147, No. 1, Nov. 1991, pp. 22-32.
Chan et al., "An Integrated ISFETs Instrumentation System in Standard CMOS Technology", IEEE Journal of Solid-State Circuits, vol. 45, No. 9, Sep. 2010, pp. 1923-1934.
Chen et al., "Silicon-based nanoelectronic field-effect pH sensor with local gate control", Applied Physics Letter, vol. 89, Nov. 2006, pp. 223512-1-223512-3.
Chen et al., "Nanoscale field effect transistor for biomolecular signal amplification", Applied Physics Letter, vol. 91, No. 24, Nov. 2007, pp. 243511-1-243511-3.
Chin et al., "Titanium Nitride Membrane Application to Extended Gate Field Effect Transistor pH Sensor Using VLSI Technology", Japanese Journal of Applied Physics, vol. 40, Part 1, No. 11, Nov. 2001, pp. 6311-6315.
Chou et al., "Simulation of Ta2O5-gate ISFET temperature characteristics", Sensor and Actuators B: Chemical, vol. 71, Nos. 1-2, Nov. 2000, pp. 73-76.
Chou et al., "Letter to the Editor on Simulation of Ta2O5-gate ISFET temperature characteristics", Sensors and Actuators B: Chemical, vol. 80, 2001, pp. 290-291.
Chung et al., "ISFET interface circuit embedded with noise rejection capability", Electronics Letters, vol. 40, No. 18, e-pub, 2 Pages, Sep. 2, 2004, pp. 1115-1116.
Chung et al., "ISFET performance enhancement by using the improved circuit techniques", Sensors and Actuators B: Chemical, vol. 113, No. 1, Jan. 2006, pp. 555-562.
Chung et al., "New ISFET interface circuit design with temperature Compensation", CiteSeerx—URL: http://citeseerx.ist.psu.edu/viewdoc/download?doi=10.1.1.95.2321&rep=rep1-&type=pdf, 2006, pp. 1.
Chung et al., "New ISFET Interface Circuit Design with Temperature Compensation", Microelectronics Journal, vol. 37, No. 10, Oct. 1, 2006, pp. 1105-1114.
Chung et al., "Temperature compensation electronics for ISFET readout applications", Biomedical Circuits and Systems, IEEE International Workshop Singapore, Dec. 1, 2004, pp. 305-308.
Dahl et al., "Circle-to-circle amplification for precise and sensitive DNA analysis," Proceedings of the National Academy of Sciences, vol. 101, No. 13, Mar. 2004, pp. 4548-4553.
Dazhong et al., "Research of CMOS Biosensor IC for Extracellular Electrophysiological Signal Recording and pH value Measuring", Solid-State and Integrated-Circuit Technology, 9th International Conference, NJ USA, Oct. 20, 2008, pp. 2557-2560.
Dorf, "The Electrical Engineering Handbook", University of California, Davis, CRC Press, 2 edition, Chapter 3—Linear Circuit Analysis, Jun. 25, 2004, pp. 3-1 to 3-66.
Eastman Kodak Company, "Image Sensor Solutions-Full-Frame CCD Image Sensor Performance Specification", www.physics.csbsju.edu/370/photometry/manuals/kaf-1001e.pdf, Feb. 19, 2001.
Eijkel et al., "Measuring Donnan-related phenomena using a solid-state ion sensor and a concentration-step method", Journal of Membrane Science, vol. 127, May 1997, pp. 203-221.
Eijkel, "Potentiometric detection and characterization of adsorbed protein using stimulus-response measurement techniques", Thesis, Sep. 3, 1955, pp. 1-147; pp. 160-192.
Eltoukhy et al., "A 0.18um CMOS 10-6 lux bioluminescence detection system-on-chip", 2004 IEEE Inti Solid States Conference. Digest of Technical Papers. Session 12, Microsystems/12.3, Feb. 17, 2004. pp. 1-3.
Eltoukhy et al., "A. 0.18-µm CMOS Bioluminescence Detection Lab-on-Chip", IEEE Journal of Solid-State Circuits, vol. 41, No. 3, Apr. 2006, pp. 651-662.
EP Extended Search report dated May 27, 2015, to EP Patent Application No. 09822323.3.
EP Extended Search report dated Nov. 7, 2017, to EP Patent Application No. 17167536.5.
EP09798251.6, Extended Search Report, dated Aug. 27, 2013, 6 pages.
EP10780930.3, Search Report, dated Jun. 15, 2015, 3 pages.
EP10780935.2, Partial Search Report, dated Jun. 9, 2015, 5 pages.
EP10780935.2, Supplementary Search Report, dated Sep. 30, 2015.
EP10857377.5, Search Report, dated Jun. 26, 2015, 3 pages.
EP11801437.2, European Search Report, dated Jul. 8, 2014.
EP11801437.2, Extended Search Report, dated Jul. 25, 2013, 10 pages.
EP11801439.8, Extended Search Report, dated Mar. 7, 2014, 9 pages.
EP11804218.3, Extended Search Report, dated Jul. 11, 2013, 3 pages.
EP11827128.7, Search Report, dated Aug. 1, 2013, 5 pages.
EP13161312.7, Extended Search Report, dated Oct. 15, 2013, 8 pages.
EP13163995.7, Extended Search Report, dated Aug. 20, 2013, 6 pages.
EP13164768.7, Extended Search Report, dated Aug. 20, 2013, 6 pages.
EP13174555.6, Extended Search Report, dated Dec. 4, 2013, 8 pages.
EP13174555.6, Search Report, dated Nov. 21, 2013, 5 pages.
EP13177039.8, Search Report, dated Nov. 21, 2013, 9 pages.
EP13177590.0, Search Report, dated Nov. 20, 2013, 5 pages.
EP14152861.2, Search Report, dated Jul. 7, 2014, 5 pages.
EP15170247.9, Search Report, dated Nov. 10, 2015, 4 pages.
Eriksson et al., "Pyrosequencing™ Technology at Elevated Temperature" Electrophoresis, vol. 25, No. 1, Jan. 2004, pp. 20-27.
Esfandyarpour et al., "Gate-controlled microfluidic chamber with magnetic bead for DNA sequencing-by-synthesis technology", Proc 5th Intl Conf Nanochannels, Microchannels and Minichannels, Puebla, Mexico, Jun. 18-20, 2007, pp. 1-5.
Faramarzpour et al., "CMOS-Based Active Pixel for Low-Light Level Detection: Analysis and Measurements", IEEE Trans Electron Devices, vol. 54, No. 12, Dec. 2007, pp. 3229-3237.
Finn et al., "Towards an Optimization of FET-Based Bio-Sensors", European Cells and Materials, vol. 4, Sup 2, 2002, pp. 21-23.
Fraden, "Handbook of Modern Sensors-Physics, Designs, and Applications", 17.3.2 CHEMFET Sensors, 1996, pp. 499-501.

(56) References Cited

OTHER PUBLICATIONS

Fritz et al., "Electronic detection of DNA by its intrinsic molecular charge", Proceedings of the National Academy of Sciences, vol. 99, No. 22, Oct. 29, 2002, pp. 14142-14146.

Gardner et al., "Enhancing electronic nose performance by sensor selection using a new integer-based genetic algorithm approach", Sensors and Actuators B: Chemical, vol. 106, No. 1, Apr. 2005, pp. 114-121.

Gracia et al., "Test Structures for ISFET Chemical Sensors", IEEE Proceedings of the 1992 International Conference on Microelectronic Test Structures, vol. 5, 1992, pp. 156-159.

Hammond et al., "A System-on-Chip Digital pH Meter for Use in a Wireless Diagnostic Capsule", IEEE Transactions on Biomedical Engineering, vol. 52, No. 4, May 2005, pp. 687-694.

Hammond et al., "Encapsulation of a liquid-sensing microchip using SU-8 photoresist", MicroElectronic Engineering, vols. 73-74, Jun. 2004, pp. 893-897.

Hammond et al., "Genomic sequencing and analysis of a Chinese Hamster ovary cell line using Illumina sequencing technology", BMC Genomics, vol. 12, No. 67, Jan. 2011, pp. 1-8.

HAMMOND P.A., et al., "Design of a Single-Chip pH Sensor Using a Conventional 0.6-μm CMOS Process," IEEE Sensors Journal, Dec. 2004, vol. 4, No. 6, pp. 706-712.

HAMMOND P.A., et al., "Performance and System-on-Chip Integration of an Unmodified CMOS ISFET," Sensors and Actuators B: Chemical, Nov. 2005, vol. 111-112, pp. 254-258.

HAN "Label-free detection of biomolecules by a field-effect transistor microarray biosensor with bio-functionalized gate surfaces," Masters Dissertation, RWTH Aachen University, 2006, pp. 1-63.

Hanshaw et al., "An indicator displacement system for fluorescent detection of phosphate oxyanions under physiological conditions", Tetrahedron Letters, vol. 45, No. 47, Nov. 15, 2004, pp. 8721-8724.

Hara et al., "Dynamic response of a Ta2O5-gate pH-sensitive field-effect transistor", Sensors Actuators B: Chemical, vol. 32, No. 2, May 1996, pp. 115-119.

Hermon et al., "Miniaturized bio-electronic hybrid for chemical sensing applications", Tech Connect News, Apr. 22, 2008, pp. 1.

Hideshima et al., "Detection of tumor marker in blood serum using antibody-modified field effect transistor with optimized BSA blocking", Sensors and Actuations B: Chemical, vol. 161, No. 1, Jan. 2012, pp. 146-150.

Hijikata et al., "Identification of a Single Nucleotide Polymorphism in the MXA Gene Promoter (T/T at nt-88) Correlated with the Response of Hepatitis C Patients to Interferon", Intervirology, vol. 43, No. 2, 2000, pp. 124-127.

Hizawa et al., "32.times.32 pH Image Sensors for Real Time Observation of Biochemical Phenomena", Transducers & Eurosensors '07, 14th Intl. Conf, on Solid-State, Actuators and Microsystems, Lyon, France, Jun. 10-14, 2007, pp. 1311-1312.

Hizawa, et al., "Sensing Characteristics of Charge Transfer Type pH Sensor by Accumulative Operation", IEEE Sensors, EXCO, Daegu, Korea, Oct. 22-25, 2006, pp. 144-147.

Hizawa T., et al., "Fabrication of a Two-dimensional pH Image Sensor Using a Charge Transfer Technique," Sensors and Actuators B: Chemical, Oct. 2006, vol. 117, No. 2, pp. 509-515.

Ingebrandt et al., "Label-free Detection of DNA using Field-Effect Transistors", Physica status solidi A, vol. 203, No. 14, Nov. 2006, pp. 3399-3411.

Izuru, "Kojien", published by Owanami, Fourth Edition, 1991, pp. 2683.

Jakobson et al., "Low frequency noise and drift in Ion Sensitive Field Effect Transistors", Sensors Actuators B: Chemical, vol. 68, Nos. 1-3, Aug. 2000, pp. 134-139.

Ji et al., "A CMOS contact imager for locating individual cells", IEEE International Symposium on Circuits and Systems, 2006, pp. 3357-3360.

Ji et al., "Contact Imaging: Simulation and Experiment", IEEE Trans Circuits Systems-I: Regular Papers, vol. 54, No. 8, 2007, pp. 1698-1710.

Kim et al., "An FET-type charger sensor for highly sensitive detection of DNA sequence", Biosensors & Bioelectronics, vol. 20, No. 1, Jul. 30, 2004, pp. 69-74.

Klein, "Time effects of ion-sensitive field-effect transistors", Sensors and Actuators, vol. 17, Nos. 1-2, May 1989, pp. 203-208.

Koch et al., "Protein detection with a novel ISFET-based zeta potential analyzer", Biosensors & Bioelectronics, vol. 14, No. 4, Apr. 1999, pp. 413-421.

Krause et al., "Extended Gate Electrode Arrays for Extracellular Signal Recordings", Sensors and Actuators B: Chemical, vol. 70, Nos. 1-3, Nov. 2000, pp. 101-107.

Kruise et al., "Detection of protein concentrations using a pH-step titration method", Sensors Actuators B: Chemical, vol. 44, Nos. 1-3, Oct. 1997, pp. 297-303.

Leamon et al., "A Massively Parallel PicoTiterPlate Based Platform for Discrete Picoliter-Scale Polymerase Chain Reactions", Electrophoresis, vol. 24, No. 21, Nov. 24, 2003, pp. 3769-3777.

Leamon J.H., et al., "Cramming More Sequencing Reactions onto Microreactor Chips," Chemical Reviews, Aug. 2007, vol. 107, No. 8, pp. 3367-3376.

Lee et al. "An Enhanced Glucose Biosensor Using Charge Transfer Techniques" Biosensors & Bioelectronics, vol. 24, No. 4, Dec. 2008, pp. 650-656.

Lee et al., "Ion-sensitive Field-Effect Transistor for Biological Sensing", Sensors, vol. 9, No. 9, 2009, pp. 7111-7131.

Li et al., "Sequence-Specific Label-Free DNA Sensors based on Silico Nanowires", Nano Letters, vol. 4, No. 2, Jan. 2004, pp. 245-247.

Ligler et al., "Array biosensor for detection of toxins", Analytical and Bioanalytical Chemistry, vol. 377, No. 3, Oct. 2003, pp. 469-477.

Lin et al., "Practicing the Novolacdeep-UV portable conformable masking technique", Journal of Vacuum Science and Technology, vol. 19, No. 4, 1981, pp. 1313-1319.

Liu et al., "An ISFET based sensing array with sensor offset compensation and pH sensitivity enhancement", IEEE International Symposium on Circuits and Systems, Jun. 2, 2010, pp. 2283-2286.

Lohrengel et al., "A new microcell or microreactor for material surface investigations at large current densities", Electrochimica Acta, vol. 49, Nos. 17-18, Jul. 2004, pp. 2863-2870.

Lui et al., "A Test Chip for ISFET/CMNOS Technology Development", IEEE International Conference on Microelectronic Test Structures, vol. 9, 1996, pp. 123-128.

Maki et al., "Nanowire-transistor based ultra-sensitive DNA methylation detection", Biosensors & Bioelectronics, vol. 23, No. 6, Jan. 2008, pp. 780-787.

Margulies M., et al., "Genome Sequencing in Microfabricated High-Density Picolitre Reactors," Nature, 2005, vol. 437, No. 7057, pp. 376-380.

Marshall et al., "DNA chips: an array of possibilities", Nature Biotechnology, vol. 16, No. 1, Jan. 1998, pp. 27-31.

Martinoia et al., "A behavioral macromodel of the ISFET in SPICE", Sensors and Actuators B: Chemical, vol. 62, No. 3, Mar. 2000, pp. 182-189.

Martinoia S., et al., "Development of ISFET Array-Based Microsystems for Bioelectrochemical Measurements of Cell Populations," Biosensors & Bioelectronics, Dec. 2001, vol. 16, Nos. 9-12, pp. 1043-1050.

Matsuo et al. "Charge Transfer Type pH Sensor with Super High Sensitivity" 14th International Conference on Solid-State Sensors Actuators and Microsystems, France, Jun. 10-14, 2007, pp. 1881-1884.

Matula, "Electrical Resistivity of Copper, Gold, Palladium, and Silver", Journal of Physical and Chemical Reference Data, vol. 8, No. 4, 1979, pp. 1147-1298.

Medoro et al., "A Lab-on-Chip for Cell Detection and Manipulation", IEEE Sensors Journal, vol. 3, No. 3, 2003, pp. 317-325.

Meyburg et al., "N-Channel field-effect transistors with floating gates for extracellular recordings", Biosensors and Bioelectronics, vol. 21, No. 7, Jan. 15, 2006, pp. 1037-1044.

Milgrew et al., "A 16x16 CMOS proton camera array for direct extracellular imaging of hydrogen-ion activity", IEEE Inti Solid-State Circuits Conference, Session 32:24, 2008, pp. 590-591, 638.

(56) References Cited

OTHER PUBLICATIONS

Milgrew et al., "A Proton Camera Array Technology for Direct Extracellular Ion Imaging", IEEE International Symposium on Industrial Electronics, 2008, pp. 2051-2055.
Milgrew et al., "Matching the transconductance characteristics of CMOS ISFET arrays by removing trapped charge", IEEE Transactions on Electronic Devices, vol. 55, No. 4, 2008, pp. 1074-1079.
Milgrew et al., "Microsensor Array Technology for Direct Extracellular Imaging", Dept Electronic and EE, University of Glasgow, Apr. 5, 2006, pp. 1-23.
Milgrew et al., "The fabrication of scalable multi-sensor arrays using standard CMOS technology", IEEE Custom Integrated Circuits Conference, 2003, pp. 513-516.
Milgrew M.J., et al., "A Large Transistor-based Sensor Array Chip for Direct Extracellular Imaging," Sensors and Actuators B: Chemical, 2005, vol. 111-112, pp. 347-353.
Milgrew M.J., et al., "The Development of Scalable Sensor Arrays Using Standard CMOS Technology," Sensors and Actuators B: Chemical, Sep. 2004, vol. 103, Nos. 1-2, pp. 37-42.
Miyahara et al., "Biochip Using Micromachining Technology", Journal of Institute of Electrostatics, Japan, vol. 27, No. 6, 2003, pp. 268-272.
Miyahara et al., "Direct Transduction of Primer Extension into Electrical Signal Using Genetic Field Effect Transistor", Micro Total Analysis Systems, vol. 1, Proceedings of UTAS 2004, 8th International Conference on Miniaturized Systems for Chemistry and Life Sciences, Malmo, Sweden, Sep. 26-30, 2004, pp. 303-305.
Miyahara et al., "Potentiometric Detection of DNA Molecules Using Field Effect Transistor", The Japan Society of Applied Physics, No. 3, 2003, pp. 1180, 30A-S2.
Morgenshtein et al., "Wheatstone-Bridge readout interface for ISFET/REFET applications", Sensors and Actuators B: Chemical, vol. 98, No. 1, Mar. 2004, pp. 18-27.
Moriizumi, "Biosensors", Oyo Buturi (monthly publication of the Japan Society of Applied Physics), vol. 54, No. 2, Feb. 10, 1985, pp. 98-114.
Naidu et al., "Introduction to Electrical Engineering", Chapter 1—Fundamental Concepts of Electricity, McGraw Hill Education (India) Private Limited, 1995, pp. 1-10.
Nakazato, "An Integrated ISFET Sensor Array", Sensors, Nov. 2009, vol. 9, No. 11, ISSN:1424-8220, [online], Internet, URL, http://www.mdpi.com/1424-8220/9/11/8831/pdf, Nov. 2009, pp. 8831-8851.
Nakazato et al., "28p-Y-7 ISFET sensor array integrated circuits based on the standard CMOS process", The 55th annual meeting of the Japan Society of Applied Physics, Book of Abstracts, Mar. 27, 2008, p. 70.
Neaman, "Electronic Circuit Analysis and Design", McGraw Hill Higher Education, 2nd Edition, Chapter 6—Basic FET Amplifiers, (reference will be uploaded in 2 parts due to size) part 1 of 2, Dec. 1, 2000, pp. 313-345.
Neaman, "Electronic Circuit Analysis and Design", McGraw Hill Higher Education, 2nd Edition, Chapter 6—Basic FET Amplifiers, (reference will be uploaded in 2 parts due to size) part 2 of 2, Dec. 1, 2000, pp. 346-381.
Nishiguchi et al., "Si nanowire ion-sensitive field-effect transistors with a shared floating gate", Applied Physics Letters, vol. 94, Apr. 2009, pp. 163106-1 to 163106-3.
Nyren et al., "Enzymatic Method for Continuous Monitoring of Inorganic Pyrophosphate Synthesis", Analytical Biochemistry, vol. 151, No. 2, Dec. 1985, pp. 504-509.
Oelßner et al., "Encapsulation of ISFET sensor chips", Sensors Actuators B: Chemical, vol. 105, No. 1, Feb. 2005, pp. 104-117.
Oelßner et al., "Investigation of the dynamic response behavior of ISFET pH sensors by means of laser Doppler velocimetry (LDV)", Sensors and Actuators B: Chemical, vol. 27, Nos. 1-3, Jun. 1995, pp. 345-348.
Offenhausser et al., "Field-Effect transistor array for monitoring electrical activity from mammalian neurons in culture", Biosensors & Bioelectronics, vol. 12, No. 8, Jan. 1997, pp. 819-826.

Ohno et al., "Electrolyte-Gated Graphene Field-Effect Transistors for Detecting pH and Protein Adsorption", Nano Letters, vol. 9, No. 9, Jul. 28, 2009, pp. 3318-3322.
Palan et al., "New ISFET sensor interface circuit for biomedical applications", Sensors and Actuators B: Chemical, vol. 57, Nos. 1-3, Sep. 1999, pp. 63-68.
Park et al., "ISFET glucose sensor system with fast recovery characteristics by employing electrolysis", Sensors and Actuators B: Chemical, vol. 83, Nos. 1-3, Mar. 15, 2002, pp. 90-97.
Patolsky et al., "Nanowire-Based Biosensors", Analytical Chemistry, vol. 78, No. 13, Jul. 1, 2006, pp. 4261-4269.
PCT/JP2005/001987, Search Report, dated Apr. 5, 2005.
PCT/JP2005/015522, Search Report, dated Sep. 27, 2005.
PCT/US2007/025721, Declaration of Non-Establishment of International Search Report, dated Jul. 15, 2008.
PCT/US2007/025721, Preliminary Report and Written Opinion on Patentability, dated Jun. 16, 2009.
PCT/US2009/003766, Search Report and Written Opinion, dated Apr. 8, 2010.
PCT/US2009/003797, Search Report and Written Opinion, dated Mar. 12, 2010.
PCT/US2009/005745, Search Report and Written Opinion, dated Dec. 11, 2009.
PCT/US2010/001543, Search Report and Written Opinion, dated Oct. 13, 2010.
PCT/US2010/001553, Search Report and Written Opinion, dated Jul. 28, 2010.
PCT/US2010/048835, Search Report and Written Opinion, dated Dec. 16, 2010.
PCT/US2011/042655, Search Report and Written Opinion, dated Oct. 21, 2011.
PCT/US2011/042660, Search Report and Written Opinion, dated Nov. 2, 2011.
PCT/US2011/042665, Search Report and Written Opinion, dated Nov. 2, 2011.
PCT/US2011/042668, Search Report and Written Opinion, dated Oct. 28, 2011.
PCT/US2011/042669, Search Report and Written Opinion, dated Jan. 9, 2012.
PCT/US2011/042683, Search Report and Written Opinion, dated Feb. 16, 2012.
PCT/US2012/058996, Search Report and Written Opinion, dated Jan. 22, 2013.
PCT/US2012/071471, Search Report and Written Opinion, dated Apr. 24, 2013.
PCT/US2012/071482, Search Report and Written Opinion, dated May 23, 2013.
PCT/US2013/022129, Search Report and Written Opinion, dated Aug. 9, 2013.
PCT/US2013/022140, Search Report and Written Opinion, dated May 2, 2013.
PCT/US2014/020887, Search Report and Written Opinion, dated May 30, 2014.
PCT/US2014/020892, Search Report and Written Opinion, dated Jun. 3, 2014.
PCT/US2014/040923, Search Report and Written Opinion, dated Sep. 1, 2014.
PCT/US2015/066052, Search Report and Written Opinion, dated Apr. 7, 2016.
Poghossian et al., "Functional testing and characterization of ISFETs on wafer level by means of a micro-droplet cell", Sensors, vol. 6, No. 4, Apr. 2006, pp. 397-404.
Pollack et al., "Genome-wide analysis of DNA copy-number changes using cDNA microarrays", Nature Genetics, vol. 23, No. 1, Sep. 1999, pp. 41-46.
Pourmand N., et al., "Direct Electrical Detection of DNA Synthesis," Proceedings of the National Academy of Sciences, Apr. 25, 2006, vol. 103, No. 17, pp. 6466-6470.
Pouthas et al., "Spatially resolved electronic detection of biopolymers", Physical Review, vol. 70, No. 3, Sep. 2004, p. 031906-1-031906-8.
Premanode et al., "A composite ISFET readout circuit employing current feedback", Sensors Actuators B: Chemical, vol. 127, No. 2, Nov. 2007, pp. 486-490.

(56) References Cited

OTHER PUBLICATIONS

Premanode et al., "A novel, low power biosensor for real time monitoring of creatinine and urea in peritoneal dialysis", Sensors and Actuators B: Chemical, vol. 120, No. 2, Jan. 2007, pp. 732-735.
Premanode et al., "Drift Reduction in Ion-Sensitive FETs using correlated double sampling", Electronics Letters, vol. 43, No. 16, Aug. 2, 2007, pp. 857-859.
Premanode et al., "Ultra-low power precision ISFET readout using global current feedback", Electronic Letters, vol. 42, No. 22, Oct. 26, 2006, pp. 1264-1265.
Purushothaman et al., "Protons and single nucleotide polymorphism detection: A simple use for the Ion Sensitive Field Effect Transistor", Sensors and Actuators B: Chemical, vol. 114, No. 2, Apr. 2006, pp. 964-968.
Purushothaman S., et al., "Towards Fast Solid State DNA Sequencing," IEEE ISCAS Proceedings, Circuits and Systems, 2002, vol. 4, pp. IV-169-IV-172.
Rodriguez-Villegas, "Solution to trapped charge in FGMOS transistors", Electronics Letters, vol. 39, No. 19, Oct. 2003, pp. 1416-1417.
Ronaghi M., et al., "A Sequencing Method Based on Real-Time Pyrophosphate," Science, Jul. 17, 1998, vol. 281, pp. 363-365.
Rothberg J.M., et al., "An Integrated Semiconductor Device Enabling Non-optical Genome Sequencing," Nature, Jul. 20, 2011, vol. 475, pp. 348-352.
Rowe et al., "An Array Immunosensor for Simultaneous Detection of Clinical Analytes", Analytical Chemistry, vol. 71, No. 2, 1999, pp. 433-439.
Sakata et al., "Cell-based field effect devices for cell adhesion analysis", Intl. Conf. on Microtechnologies in Medicine and Biology, May 9-12, 2006, Okinawa, Japan, 2006, pp. 177-179.
Sakata et al., "Detection of DNA recognition events using multi-well field effect transistor", Biosensors & Bioelectronics, vol. 21, 2005, pp. 827-832.
Sakata et al., "Detection sensitivity of genetic field effect transistor combined with charged nanoparticle-DNA conjugate", Intl. Conf. on Microtechnologies in Medicine and Biology, May 9-12, 2005, Okinawa, Japan, 2006, pp. 97-100.
Sakata et al., "Direct detection of single nucleotide polymorphism using genetic field effect transistor", International Microprocesses and Nanotechnology Conference. Oct. 26-29, 2004, Osaka, Japan. Digest of Papers Microprocesses and Nanotechnology 2004. pp. 226-227.
Sakata et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, pp. 219-222.
Sakata et al., "Direct transduction of allele-specific primer extension into electrical signal using genetic field effect transistor", Biosensors & Bioelectronics, vol. 22, 2007, pp. 1311-1316.
Sakata et al., "DNA Analysis Chip Based on Field-Effect Transistors", Japanese Journal of Applied Physics, vol. 44, No. 4B, 2005, pp. 2854-2859.
Sakata et al., "DNA Sequencing Using Genetic Field Effect Transistor", 13th International Conference on Solid-State sensors, Actuators and Microsystems, vol. 2, Jun. 5-9, 2005, Seoul, Korea, pp. 1676-1679.
Sakata et al., "Immobilization of oligonucleotide probes on Si3N4 surface and its application to genetic field effect transistor", Materials Science and Engineering: C, vol. 24, Nos. 6-8, Dec. 2004, pp. 827-832.
Sakata et al., "Potential Behavior of Biochemically Modified Gold Electrode for Extended-Gate Field-Effect Transistor", Japanese Journal of Applied Physics, vol. 44, Part 1, No. 4S, Apr. 2005, pp. 2860-2863.
Sakata et al., "Potential response of genetic field effect transistor to charged nanoparticle-DNA conjugate", International Microprocesses and Nanotechnology Conference. Oct. 25-28, 2005. Tokyo, Japan. Digest of Papers Microprocesses and Nanotechnology 2005. pp. 42-43.
Sakata et al., "Potentiometric Detection of Allele Specific Oligonucleotide Hybridization Using Genetic Field Effect Transistor", Micro Total Analysis Systems, vol. 1,8th Intl. Conf. on Miniaturized Systems for Chemistry and Life Sciences, Sep. 26-30, 2004, Malmo, Sweden, pp. 300-302.
Sakata et al., "Potentiometric Detection of DNA Molecules Hybridization Using Gene Field Effect Transistor and Intercalator", Materials Research Society Symposium Proceedings, vol. 782, Micro- and Nanosystems, Boston, Massachusetts, Jan. 2003, pp. 393-398.
Sakata et al., "Potentiometric Detection of DNA Using Genetic Transistor", Denki Gakkai Kenkyukai Shiryo Chemical Sensor Kenkyukai, CHS-03-51-55, 2003, pp. 1-5.
Sakata et al., "Potentiometric Detection of Single Nucleotide Polymorphism by Using a Genetic Field-effect transistor", ChemBioChem, vol. 6, No. 4, Apr. 2005, pp. 703-710.
Sakata T., et al., "DNA Sequencing Based on Intrinsic Molecular Charges," Angewandte Chemie International, Mar. 27, 2006, vol. 45, No. 14, pp. 2225-2228.
Sakurai T., et al., "Real-Time Monitoring of DNA Polymerase Reactions by a Micro ISFET pH Sensor," Analytical Chemistry, Sep. 1992, vol. 64, No. 17, pp. 1996-1997.
Salama, "CMOS luminescence detection lab-on-chip: modeling, design, and characterization", Thesis, Presented at Stanford University, 2005, pp. ii-78.
Salama, "Modeling and simulation of luminescence detection platforms", Biosensors & Bioelectronics, vol. 19, No. 11, Jun. 15, 2004, pp. 1377-1386.
Sawada et al., "A novel fused sensor for photo- and ion-sensing", Sensors and Actuators B: Chemical, vol. 106, No. 2, May 2005, pp. 614-618.
Sawada et al., "Highly sensitive ion sensors using charge transfer technique", Sensors and Actuators B: Chemical, vol. 98, No. 1, Mar. 2004, pp. 69-72.
Schasfoort et al., "A new approach to ImmunoFET operation", Biosensors & Bioelectronics, vol. 5, No. 2, 1990, pp. 103-124.
Schasfoort et al., "Field-effect flow control for microfabricated fluidic networks", Science, vol. 286. No. 5441, Oct. 29, 1999, pp. 942-945.
Schoning et al., "Bio FEDs (Field-Effect Devices): State-of-the-Art and New Directions", Electroanalysis, vol. 18, Nos. 19-20, Sep. 2006, pp. 1893-1900.
Schroder, "6. Oxide and Interface Trapped Charges, Oxide Thickness", Semiconductor Material and Device Characterization, John Wiley & Sons, ISBN: 978-0-471-73906-7, Feb. 2006, pp. 319-387.
Seong-Jin et al. "Label-Free CMOS DNA Quantification With On-Chip Noise Reduction Schemes" Solid-State Sensors, Actuators and Microsystems Conference, IEEE, Jun. 10, 2013, pp. 947-950.
Shah, "Microfabrication of a parellelrray DNA pyrosequencing chip", NNIN REU Research Accomplishments, 2005, pp. 130-131.
Shepherd et al., "A biochemical translinear principle with weak inversion ISFETs", IEEE Trans Circuits Syst-I, vol. 52, No. 12, Dec. 2005, pp. 2614-2619.
Shepherd et al., "A novel voltage-clamped CMOS ISFET sensor interface", IEEE, 2007, pp. 3331-3334.
Shepherd et al., "Towards direct biochemical analysis with weak inversion ISFETS", Intl Workshop on Biomedical, 2004, pp. S1.5-5-S1.5-8.
Shepherd et al., "Weak inversion ISFETs for ultra-low power biochemical sensing and real-time analysis", Sensors Actuators B, vol. 107, 2005, pp. 468-473.
Shi et al., "Radical Capillary Array Electrophoresis Microplace and Scanner for High-Performance Nucleic Acid Analysis", Analytical Chemistry, vol. 71, No. 23, 1999, pp. 5354-5361.
Simonian et al., "FET based biosensors for the direct detection of organophosphate neurotoxins", Electroanalysis, vol. 16, No. 22, 2004, pp. 1896-1906.
Souteyrand et al., "Direct detection of the hybridization of synthetic homo-oligomer DNA sequences by field effect", Journal of Physical Chemistry B, vol. 101, No. 15, 1997, pp. 2980-2985.
Starodub et al., "Immunosensor for the determination of the herbicide simazine based on an ion-selective field-effect transistor", Analytica Chimica Acta, vol. 424, No. 1, Nov. 2000, pp. 37-43.

(56) References Cited

OTHER PUBLICATIONS

Takenaka et al., "DNA Sensing on a DNA Probe-Modified Electrode Using Ferrocenylnaphthalene Dimide as the Electrochemically Active Ligand", Analytical Chemistry, vol. 72. No. 6, 2000, pp. 1334-1341.
Temes et al., "A Tutorial Discussion of the Oversampling Method for A/D and D/A Conversion", IEEE International Symposium on Circuits and Systems, vols. 2 of 4, 1990, 5 pages.
Thewes et al., "CMOS-based Biosensor Arrays", Proceedings of the Design, Automation and Test in Europe Conference and Exhibition, 2005, 2 pages.
Tokuda et al., "A CMOS image sensor with optical and potential dual imaging function for on-chip bioscientific applications", Sensors and Actuators A: Physical, vol. 125, No. 2, Jan. 2006, pp. 273-280.
Tomaszewski et al., "Electrical characterization of ISFETs", Journal of Telecommunications and Information Technology, Mar. 2007, pp. 55-60.
Toumazou et al., "Using transistors to linearise biochemistry," Electronics Letters, vol. 43, No. 2, Jan. 18, 2007, 3 pages.
Truman et al. "Monitoring liquid transport and chemical composition in lab on a chip systems using ion sensitive FET devices", Lab on a Chip, vol. 6, No. 9, Jul. 2006, pp. 1220-1228.
Unknown, "ISFET Wikipedia article", Wikipedia, Last modified Nov. 7, 2006.
Unknown, "OV5640 Datasheet Product Specification", 1/4" color CMOS QSXGA (5 megapixel) image sensor with OmniBSI technology. May 1, 2011, p. 1, line 9 and pp. 2-7, paragraph 1.
Uslu et al., "Labelfree fully electronic nucleic acid detection system based on a fieldeffect transistor device", Biosensors and Bioelectronics, vol. 19. No. 12, Jul. 2004, pp. 1723-1731.
Van Der Schoot et al., "The Use of a Multi-ISFET Sensor Fabricated in a Single Substrate", Sensors and Actuators, vol. 12, No. 4, Nove.-Dec. 1987, pp. 463-468.
Van Der Wouden et al., "Directional flow induced by synchronized longitudinal and zeta-potential controlling AC-electrical fields", Lab Chip, vol. 6, No. 10, Oct. 2006, pp. 1300-1305.
Van Hal et al., "A general model to describe the electrostatic potential at electrolyte oxide interfaces", Advances in Colloid and Interface Science, vol. 69, Nos. 1-3, Dec. 1996, pp. 31-62.
Van Kerkhof, "Development of an ISFET based heparin sensor using the ion-step measuring method", Biosensors & Bioelectronics, vol. 8, Nos. 9-10, 1993, pp. 463-472.
Van Kerkhof et al., "ISFET Responses on a stepwise change in electrolyte concentration at constant pH", Sensors Actuators B: Chemical, vol. 18-19, Mar. 1994, pp. 56-59.
Van Kerkhof et al., "The development of an ISFET-based heparin sensor," Thesis 1994. Published Aug. 10, 1965.
Van Kerkhof et al., "The ISFET based heparin sensor with a monolayer of protamine as affinity ligand", Biosensors & Bioelectronics, vol. 10, Nos. 3-4, 1995, pp. 269-282.

Vardalas, "Twists and Turns in the Development of the Transistor", IEEE—USA Today's Engineer Online, May 2003, 6 pages.
Voigt et al., "Diamond-like carbon-gate pH-ISFET", Sensors and Actuators B: Chemical, vol. 44, Nos. 1-3, Oct. 1997, pp. 441-445.
Wagner et al., "All-in-one solid-state device based on a light-addressable potentiometric sensor platform", Sensors and Actuators B: Chemical, vol. 117, No. 2, Oct. 2006, pp. 472-479.
Wang et al., "Label-free detection of small-molecule-protein interactions by using nanowire nanosensors", Proceedings of the National Academy of Sciences, vol. 102, No. 9, Mar. 2005, pp. 3208-3212.
Wilhelm et al., "pH Sensor Based on Differential Measurements on One pH-FET Chip", Sensors and Actuators B: Chemical, vol. 4, Nos. 1-2, May 1991, pp. 145-149.
Woias et al., "Slow pH response effects of silicon nitride ISFET sensors", Sensors and Actuators B: Chemical, vol. 48, Nos. 1-3, May 1998, pp. 501-504.
Woias P., et al., "Modelling the Short-Time Response of ISFET Sensors," Sensors and Actuators B: Chemical, Mar. 1995, vol. 24, Nos. 1-3, pp. 211-217.
Wood et al., "Base composition-independent hybridization in tetramethylammonium chloride: a method for oligonucleotide screening of highly complex gene libraries", Proceedings of the National Academy of Sciences, vol. 82, No. 6, Mar. 1985, pp. 1585-1588.
Wu et al., "DNA and protein microarray printing on silicon nitride waveguide surfaces", Biosensors & Bioelectronics, vol. 21, No. 7, Jan. 2006, pp. 1252-1263.
Xu et al., "Analytical Aspects of FET-Based Biosensors", Frontiers in Bioscience, vol. 10, Jan. 2005, pp. 420-430.
Yeowt.C.W., et al., "A Very Large Integrated pH-ISFET Sensor Array Chip Compatible with Standard CMOS Processes," Sensor and Actuators B: Chemical, Oct. 1997, vol. 44, Nos. 1-3, pp. 434-440.
Yoshida et al., "Development of a Wide Range pH Sensor based on Electrolyte-Insulator-Semiconductor Structure with Corrosion-Resistant Al2O3—Ta2O5 and Al2O3—ZrO2", Journal of the Electrochemical Society, vol. 151, No. 3, 2004, pp. H53-H58.
Yuqing et al., "Ion sensitive field effect transducer-based biosensors", Biotechnology Advances, vol. 21, No. 6, Sep. 2003, pp. 527-534.
Zhang et al., "32-Channel Full Customized CMOS Biosensor Chip for Extracellular neural Signal Recording", Proc. of the 2nd Intl. IEEE EMBs Conf. on Neural Engineering, Arlington, Virginia, Mar. 16-19, 2005, pp. v-viii.
Zhao et al., "Floating-Gate Ion Sensitive Field-Effect Transistor for Chemical and Biological Sensing", MRS Proceedings, vol. 828, 2005, pp. 349-354.
Zhou et al., "Quantitative detection of single nucleotide polymorphisms for a pooled sample by a bioluminometric assay coupled with modified primer extension reactions (BAMPER)", Nucleic Acids Research, vol. 29, No. 19, Oct. 2001, (e93), 1-11.

\* cited by examiner

CHEMICAL SENSOR ARRAY HAVING MULTIPLE SENSORS PER WELL

RELATED APPLICATION

This application is a continuation of U.S. application Ser. No. 17/070,142, filed Oct. 14, 2020. U.S. application Ser. No. 17/070,142 is divisional of U.S. application Ser. No. 16/663,052, filed Oct. 24, 2019; which is issued as U.S. Pat. No. 10,816,504 on Oct. 27, 2020. U.S. Pat. No. 10,816,504 is a divisional of U.S. application Ser. No. 14/293,247 filed Jun. 2, 2014; which issued as U.S. Pat. No. 10,458,942 on Oct. 29, 2019. U.S. Pat. No. 10,458,942 claims benefit of U.S. Provisional Application No. 61/833,375 filed Jun. 10, 2013. The entire contents of the aforementioned applications are incorporated by reference herein, each in its entirety.

BACKGROUND

The present disclosure relates to sensors for chemical analysis, and to methods for manufacturing such sensors.

A variety of types of chemical sensors have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect and/or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, due to the protonation or deprotonation of surface charge groups caused by the ions present in the analyte solution. The change in surface potential at the sensitive area of the ISFET affects the threshold voltage of the device, which can be measured to indicate the presence and/or concentration of ions within the solution.

Arrays of ISFETs may be used for monitoring chemical reactions, such as DNA sequencing reactions, based on the detection of ions present, generated, or used during the reactions. See, for example, U.S. Pat. No. 7,948,015 to Rothberg et al., which is incorporated by reference herein. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring neural activity, nucleic acid sequencing, etc.

An issue that arises in the operation of large scale chemical sensor arrays is the susceptibility of the sensor output signals to noise. Specifically, the noise affects the accuracy of the downstream signal processing used to determine the characteristics of the chemical and/or biological process being detected by the sensors.

It is therefore desirable to provide devices including low noise chemical sensors, and methods for manufacturing such devices.

SUMMARY

In one embodiment, a device is described. The device includes a material defining a reaction region. The device also includes a plurality of chemically-sensitive field effect transistors have a common floating gate in communication with the reaction region. The device also includes a circuit to obtain individual output signals from the chemically-sensitive field effect transistors indicating an analyte within the reaction region.

In another embodiment, a method for manufacturing a device is described. The method includes forming a material defining a reaction region. The method further includes forming a plurality of chemically-sensitive field effect transistors having a common floating gate in communication with the reaction region. The method further includes forming a circuit to obtain individual output signals from the chemically-sensitive field effect transistors indicating an analyte within the reaction region.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

A chemical detection device is described that includes multiple chemical sensors for concurrently detecting a chemical reaction within the same, operationally associated reaction region. The multiple sensors can provide redundancy, as well as improved accuracy in detecting characteristics of the chemical reaction.

By utilizing multiple chemical sensors to separately detect the same chemical reaction, the individual output signals can be combined or otherwise processed to produce a resultant, low noise output signal. For example, the individual output signals can be averaged, such that the signal-to-noise ratio (SNR) of the resultant output signal is increased by as much as the square root of the number of individual output signals. In addition, the resultant output signal can compensate for differences among the values of the individual output signals, caused by variations in chemical sensor performance which could otherwise complicate the downstream signal processing. As a result of the techniques described herein, low-noise chemical sensor output signals can be provided, such that the characteristics of reactions can be accurately detected.

Figure 1:
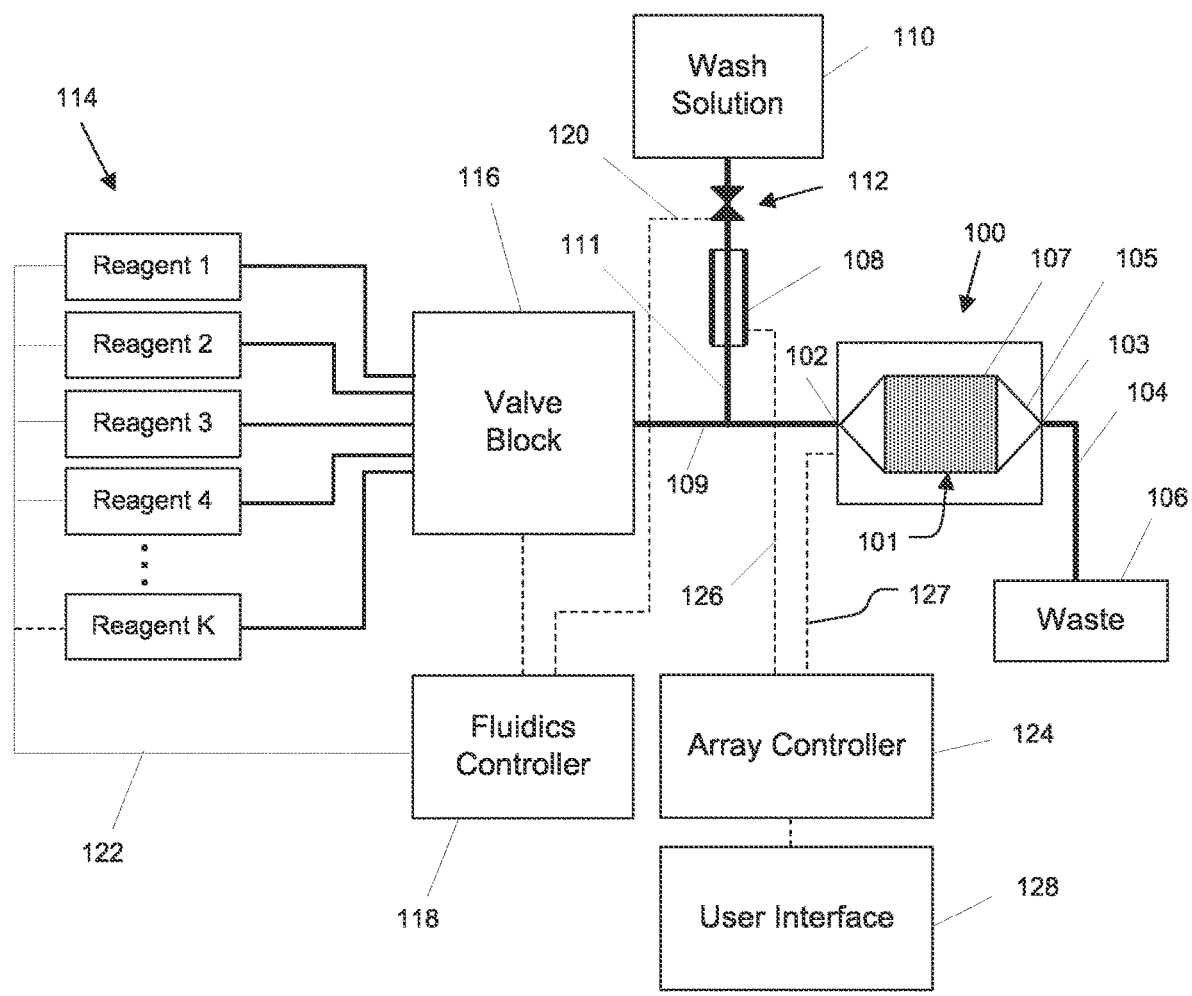
FIG. 1 illustrates a block diagram of components of a system for nucleic acid sequencing.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 of reaction regions overlying groups of chemical sensors of a sensor array as described herein. The flow cell 101 includes an inlet 102, an outlet 103, and a flow chamber 105 defining a flow path of reagents over the microwell array 107.

The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes reaction regions, also referred to herein as microwells, which are operationally associated with chemical sensors of the sensor array. As described in more detail below, each reaction region is operationally associated with multiple chemical sensors suitable for detecting an analyte or reaction of interest within that reaction region. These multiple chemical sensors can provide redundancy, as well as improved detection accuracy. The microwell array 107 may be integrated in the integrated circuit device 100, so that the microwell array 107 and the sensor array are part of a single device or chip.

In exemplary embodiments described below, groups of four chemical sensors are coupled to each of the reaction regions. Alternatively, the number of chemical sensors operationally associated with a single reaction region may be different than four. More generally, two or more chemical sensors may be operationally associated with a single reaction region.

The flow cell 101 may have a variety of configurations for controlling the path and flow rate of reagents 114 over the microwell array 107. The array controller 124 provides bias voltages and timing and control signals to the integrated circuit device 100 for reading the chemical sensors of the sensor array as described herein. The array controller 124 also provides a reference bias voltage to the reference electrode 108 to bias the reagents 114 flowing over the microwell array 107.

During an experiment, the array controller 124 collects and processes individual output signals from the chemical sensors of the sensor array through output ports on the integrated circuit device 100 via bus 127. As described in more detail below, this processing can include calculating a resultant output signal for a group of sensors as a function of the individual output signals from the chemical sensors in the group. The array controller 124 may be a computer or other computing means. The array controller 124 may include memory for storage of data and software applications, a processor for accessing data and executing applications, and components that facilitate communication with the various components of the system in FIG. 1.

In the illustrated embodiment, the array controller 124 is external to the integrated circuit device 100. In some alternative embodiments, some or all of the functions performed by the array controller 124 are carried out by a controller or other data processor on the integrated circuit device 100. In yet other embodiments, a combination of resources internal and external to the integrated circuit device 100 is used to obtain the individual output signals and calculate the resultant output signal for a group of sensors using the techniques described herein.

The value of a resultant output signal for a group of chemical sensors indicates physical and/or chemical characteristics of one or more reactions taking place in the corresponding reaction region. For example, in an exemplary embodiment, the values of the resultant output signals may be further processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No 61/428,097, filed Dec. 29, 2010, each of which are incorporated by reference herein.

The user interface 128 may display information about the flow cell 101 and the output signals received from chemical sensors of the sensor array on the integrated circuit device 100. The user interface 128 may also display instrument settings and controls, and allow a user to enter or set instrument settings and controls.

The fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors indicating chemical reactions occurring in response to the delivery of the reagents 114.

During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figure 2:
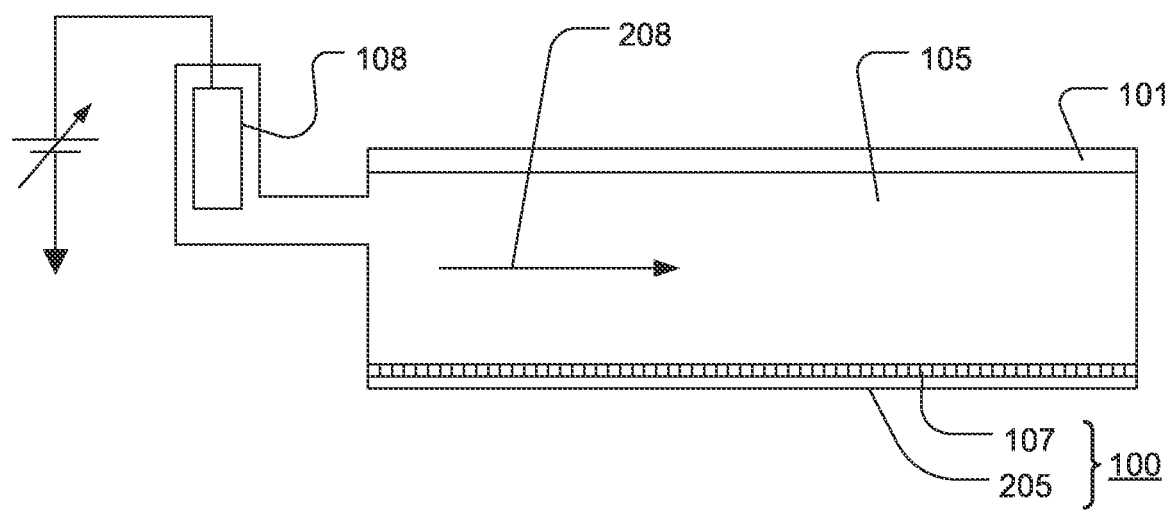
FIG. 2 illustrates cross-sectional and expanded views of a portion of an integrated circuit device and flow cell.

FIG. 2 illustrates cross-sectional and expanded views of a portion of the integrated circuit device 100 and flow cell 101. The integrated circuit device 100 includes the microwell array 107 of reaction regions operationally associated with sensor array 205. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed.

The chemical sensors of the sensor array 205 are responsive to (and generate output signals related to) chemical reactions within associated reaction regions in the microwell array 107 to detect an analyte of interest. The chemical sensors of the sensor array 205 may for example be chemically sensitive field-effect transistors (chemFETs), such as ion-sensitive field effect transistors (ISFETs). Examples of chemical sensors and array configurations that may be used in embodiments are described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

Figure 3:
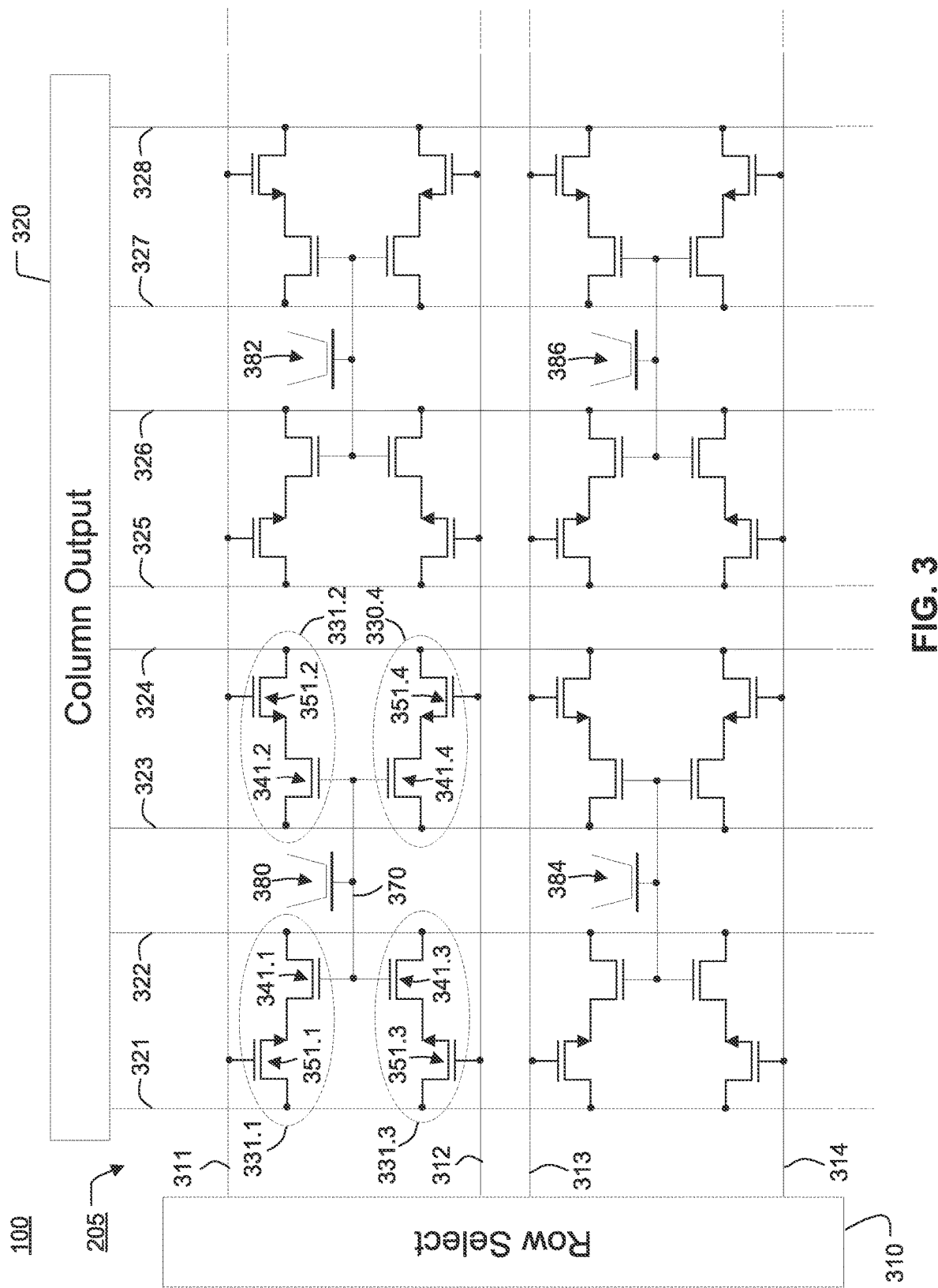
FIG. 3 illustrates a schematic diagram of a portion of the integrated circuit device 100 including a sensor array having multiple chemical sensors coupled to the same reaction region.

FIG. 3 illustrates a schematic diagram of a portion of the integrated circuit device 100 including sensor array 205 having multiple chemical sensors coupled to the same reaction region. In the illustrated embodiment, sixteen chemical sensors and four reaction regions are illustrated, representing a small section of the sensor array 205 and microwell array 107 that can include millions of chemical sensors and reaction regions.

The integrated circuit device 100 includes an access circuit for accessing the chemical sensors of the sensor array 205. In the illustrated example, the access circuit includes a row select circuit 310 coupled to the sensor array 205 via row lines 311-314. The access circuit also includes column output circuit 320 coupled to the sensor array 205 via column lines 321-328.

The row select circuit 310 and the column output circuit 320 are responsive to timing and control signals provided by the array controller 124 in FIG. 1 to select the various chemical sensors and operate the sensor array 205 as described below. The array controller 124 also provides a reference bias voltage to the reference electrode (See, FIG. 1, reference numeral 108) to bias the reagents flowing across open ends of the reaction regions 380, 382, 384, 386 of the microwell array 107 during operation.

In the illustrated embodiment, groups of four chemical sensors are operationally associated with each of the reaction regions 380, 382, 384, 386. Alternatively, the number of chemical sensors operationally associated with a single reaction region may be different than four. More generally, two or more chemical sensors may be operationally associated with a single reaction region. In some embodiments, the number of chemical sensors operationally associated with a single reaction region may be greater than four, such as sixteen or more.

The group containing chemical sensors 331.1-331.4 is representative of the groups of sensors of the sensor array 205. In the illustrated embodiment, each chemical sensor 331.1-331.4 includes a chemically-sensitive field effect transistor 341.1-341.5 and a row select switch 351.1-351.4.

The chemically-sensitive field effect transistors 341.1-341.4 have a common floating gate 370 in communication with the reaction region 380. That is, the common floating gate 370 is coupled to channels of each of the chemically-sensitive field effect transistors 341.1-341.5. The chemically-sensitive field effect transistors 341.1-341.5 may each include multiple patterned layers of conductive elements within layers of dielectric material.

The common floating gate 370 may for example include an uppermost conductive element (referred to herein as a sensor plate) that defines a surface (e.g. a bottom surface) of the reaction region 380. That is, there is no intervening deposited material layer between the uppermost electrical conductor and the surface of the reaction region 380. In some alternative embodiments, the uppermost conductive element of the common floating gate 370 is separated from the reaction region 380 by a deposited sensing material (discussed in more detail below).

In operation, reactants, wash solutions, and other reagents may move in and out of the reaction region 380 by a diffusion mechanism. The chemical sensors 331.1-331.4 are each responsive to (and generate individual output signals related to) chemical reactions within the reaction region 380 to detect an analyte or reaction property of interest. Changes in the charge within the reaction region 380 cause changes in the voltage on the common floating gate 370, which in turn changes the individual threshold voltages of each of the chemically-sensitive field effect transistors 341.1-341.4 of the sensors 331.1-331.4.

In a read operation of a selected chemical sensor 331.1, the row select circuit 310 facilitates providing a bias voltage to row line 311 sufficient to turn on row select transistor 351.1. Turning on the row select transistor 351.1 couples the drain terminal of the chemically-sensitive transistor 341.1 to the column line 321. The column output circuit 320 facilitates providing a bias voltage to the column line 321, and providing a bias current on the column line 321 that flows through the chemically-sensitive transistor 341.1. This in turn establishes a voltage at the source terminal of the chemically-sensitive transistor 341.1, which is coupled to the column line 322. In doing so, the voltage on the column line 322 is based on the threshold voltage of the chemically-sensitive transistor 341.1, and thus based on the amount of charge within the reaction region 380. Alternatively, other techniques may be used to read the selected chemical sensor 331.1.

The column output circuit 320 produces an individual output signal for the chemically-sensitive transistor 341.1 based on the voltage on the column line 322. The column output circuit 320 may include switches, sample and hold capacitors, current sources, buffers, and other circuitry used to operate and read the chemical sensors, depending upon the array configuration and read out technique. In some embodiments, the column output circuit 320 may include circuits such as those described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, which were incorporated by reference above.

The individual output signals of the other chemical sensors 331.2-331.4 coupled to the reaction region 380 can be read out in a similar fashion. In doing so, the column output circuit 320 produces individual output signals for each of the chemical sensors 331.1-331.4.

The individual output signals for each of the chemical sensors 331.1-331.4 can then be combined or otherwise processed by the array controller 124 (or other data processor) to calculate a resultant, low noise output signal for the group of chemical sensors 331.1-331.4. For example, the resultant output signal may be an average of the individual output signals. In such a case, the SNR of the resultant output signal can be increased by as much as the square root of the number of individual output signals. In addition, the resultant output signal can compensate for differences among the values of the individual output signals, caused by variations in performance of the chemical sensors 331.1-331.4 which could otherwise complicate the downstream signal processing.

Figure 4:
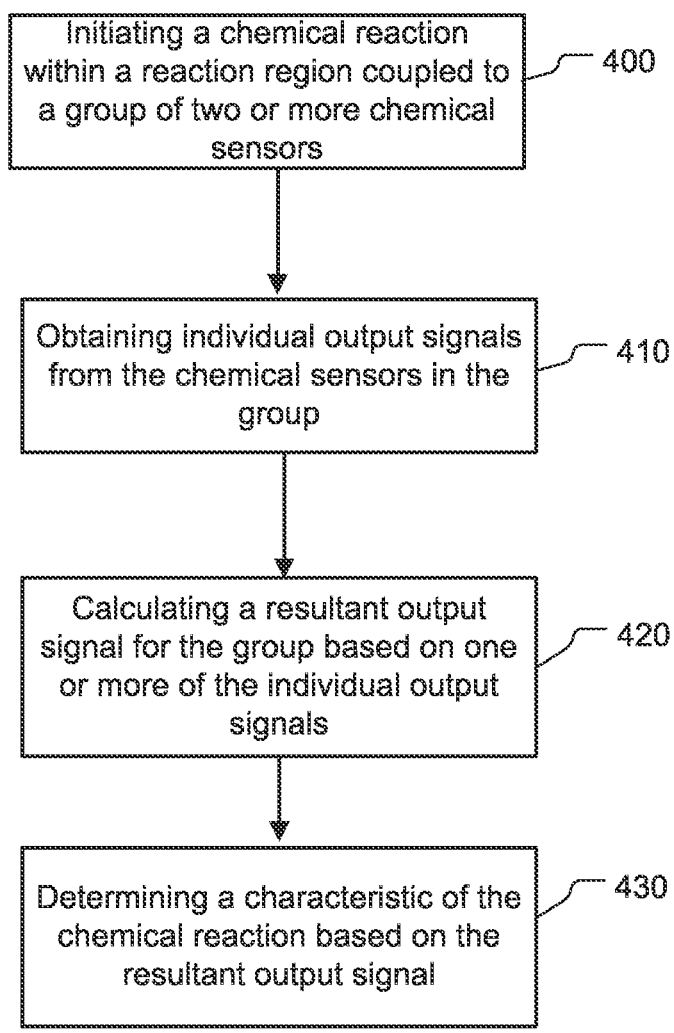
FIG. 4 is a flow chart of an example process for calculating a resultant output signal for a group of chemical sensors coupled to a single reaction region.

FIG. 4 is a flow chart of an example process for calculating a resultant output signal for a group of chemical sensors coupled to a single reaction region. Other embodiments may perform different or additional steps than the ones illustrated in FIG. 4. For convenience, FIG. 4 will be described with reference to a system that performs a process. The system can be for example, the system of FIG. 1.

At step 400, a chemical reaction is initiated within a reaction region coupled to a group of two or more chemical sensors. The group of chemical sensors may for example include respective chemically-sensitive field effect transistors having a common floating gate in communication with the reaction region, as described above with respect to FIG. 3. The chemical reaction may be a sequencing reaction, as described above.

At step 410, individual output signals are obtained from the chemical sensors in the group. The individual output signals may for example be obtained by selecting and reading out the individual chemical sensors using the techniques described above. In some embodiments, flowing of reagent(s) causes chemical reactions within the reaction region that release hydrogen ions, and the amplitude of the individual output signals from the chemical sensors is related to the amount of hydrogen ions detected.

At step 420, a resultant output signal for the group is calculated based on one or more of the individual output signals. The resultant output signal may for example be an average of the individual output signals. Alternatively, other techniques may be used to calculate the resultant output signal.

At step 430, a characteristic of the chemical reaction is determined based on the resultant output signal. For example, the characteristic of the chemical reaction may be determined based on the value of the resultant output signal using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No 61/428,097, filed Dec. 29, 2010, each of which were incorporated by reference above.

Figure 5:
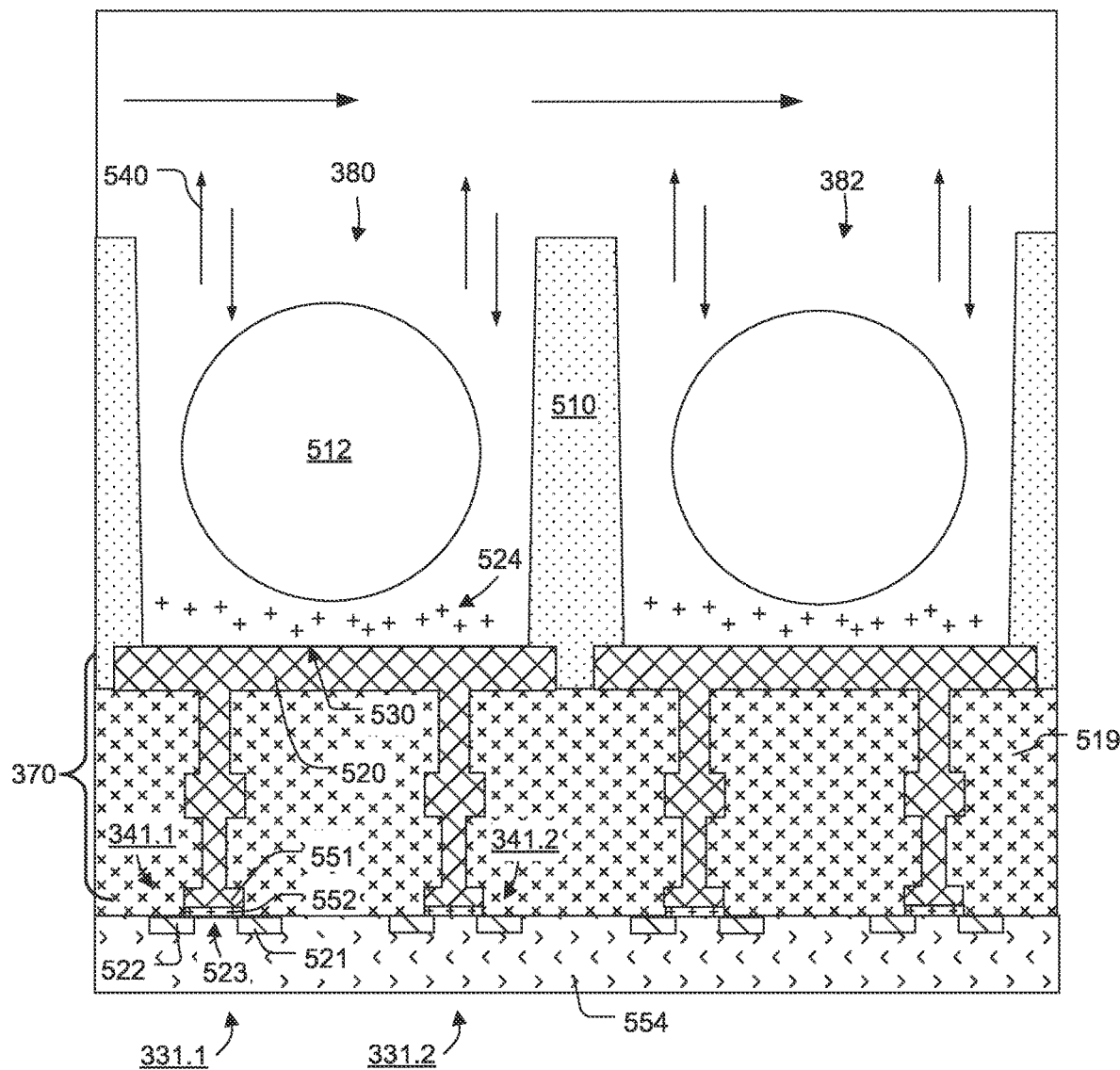
FIG. 5 illustrates a cross-sectional view of portions of two groups of chemical sensors and their corresponding reaction regions according to a first embodiment.

FIG. 5 illustrates a cross-sectional view of portions of two groups of chemical sensors and their corresponding reaction regions according to a first embodiment. In FIG. 5, the chemically-sensitive field effect transistors 341.1, 341.2 of the chemical sensors 331.1, 331.2 in the group of sensors 331.1-331.4 coupled to the reaction region 380 are visible. The chemically-sensitive field effect transistors 341.3, 341.4 of the other chemical sensors 331.3, 331.4 in the group lie behind this cross-section. Similarly, the cross-section of FIG. 5 shows the chemically-sensitive field effect transistors of two chemical sensors in the group of chemical sensors that is coupled to the adjacent reaction region 382. In this illustration, the select switches of the chemical sensors, access lines and other connections are omitted for simplicity.

The chemical sensor 331.1 is representative of the group of chemical sensors 331.1-331.4. In the illustrated example, the chemically-sensitive field effect transistor 341.1 of the chemical sensor 331.1 is a chemically-sensitive field effect transistor (chemFET), more specifically an ion-sensitive field effect transistor (ISFET) in this example.

The chemically-sensitive field effect transistor 341.1 includes common floating gate 370 having a conductive element 520 coupled to the reaction region 380. The conductive element 520 is the uppermost floating gate conductor (also referred to herein as a sensor plate) in the common floating gate 370. In the embodiment illustrated in FIG. 5, the common floating gate 370 includes multiple patterned layers of conductive material within layers of dielectric material 519.

In FIG. 5, the conductive element 520 electrically connects individual multi-layer floating gate structures that extend over the channel regions of each of the chemically-sensitive field effect transistors 341.1-341.4 of the group of chemical sensors 331.1-331.4. In doing so, the common floating gate 370 is shared among the chemical sensors 331.1-331.4.

The chemically-sensitive field effect transistor 341.1 includes a source region 521 and a drain region 522 within a semiconductor substrate 354. The source region 521 and the drain region 522 comprise doped semiconductor material having a conductivity type different from the conductivity type of the substrate 554. For example, the source region 521 and the drain region 522 may comprise doped P-type semiconductor material, and the substrate may comprise doped N-type semiconductor material.

Channel region 523 separates the source region 521 and the drain region 522. The common floating gate 370 includes a conductive element 551 separated from the channel region 523 by a gate dielectric 552. The gate dielectric 552 may be for example silicon dioxide. Alternatively, other dielectrics may be used for the gate dielectric 552.

As shown in FIG. 5, the reaction region 380 is within an opening extending through dielectric material 510 to the upper surface of the conductive element 520. The dielectric material 510 may comprise one or more layers of material, such as silicon dioxide or silicon nitride. The opening in the dielectric material 510 may for example have a circular cross-section. Alternatively, the opening may be non-circular. For example, the cross-section may be square, rectangular, hexagonal, or irregularly shaped. The dimensions of the openings within the dielectric material 510, and their pitch, can vary from embodiment to embodiment.

In the illustrated embodiment, the upper surface 530 of the conductive element 520 is the bottom surface of the reaction region 380. That is, there is no intervening deposited material layer between the upper surface 530 of the conductive element 520 and the reaction region 380. As a result of this structure, the upper surface 530 of the conductive element 520 acts as the sensing surface for the group of chemical sensors 331.1-331.4. The conductive element 520 may comprise one or more of a variety of different materials to facilitate sensitivity to particular ions (e.g. hydrogen ions).

During manufacturing and/or operation of the device, a thin oxide of the electrically conductive material of the conductive element 520 may be grown on the upper surface 530 which acts as a sensing material (e.g. an ion-sensitive sensing material) for the group of chemical sensors 331.1-331.4. For example, in one embodiment the conductive element 520 may be titanium nitride, and titanium oxide or titanium oxynitride may be grown on the upper surface 530 during manufacturing and/or during exposure to solutions during use. Whether an oxide is formed depends on the conductive material, the manufacturing processes performed, and the conditions under which the device is operated.

In the illustrated example, the conductive element 520 is shown as a single layer of material. More generally, the conductive element 520 may comprise one or more layers of a variety of electrically conductive materials, such as metals or ceramics, depending upon the embodiment. The conductive material can be for example a metallic material or alloy thereof, or can be a ceramic material, or a combination thereof. An exemplary metallic material includes one of aluminum, copper, nickel, titanium, silver, gold, platinum, hafnium, lanthanum, tantalum, tungsten, iridium, zirconium, palladium, or a combination thereof. An exemplary ceramic material includes one of titanium nitride, titanium aluminum nitride, titanium oxynitride, tantalum nitride, or a combination thereof.

In some alternative embodiments, an additional conformal sensing material (not shown) is deposited on the sidewall of the opening in the dielectric material 510 and on the upper surface 530 of the sensor plate 520. In such a case, an inner surface of the deposited sensing material defines the reaction region 380. The sensing material may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the embodiment.

In operation, reactants, wash solutions, and other reagents may move in and out of the reaction region 580 by a diffusion mechanism 540. Each of the chemical sensors 331.1-331.4 are responsive to (and generates an output signal related to) the amount of charge 524 proximate to the conductive element 520. The presence of charge 524 in an analyte solution alters the surface potential at the interface between the analyte solution and the conductive element 520, due to the protonation or deprotonation of surface charge groups. Changes in the charge 524 cause changes in the voltage on the floating gate structure 518, which in turn changes in the threshold voltages of the chemically-sensitive transistors 341.1-341.4 of each of the chemical sensors 331.1-331.4. The respective changes in threshold voltages can be measured by measuring the current through the respective channel regions (e.g. channel region 523 of sensor 331.1). As a result, each of the chemical sensors 331.1-331.4 can be operated to provide individual current-based or voltage-based output signals on an array line connected to its corresponding source region or drain region.

In an embodiment, reactions carried out in the reaction region 380 can be analytical reactions to identify or determine characteristics or properties of an analyte of interest. Such reactions can directly or indirectly generate byproducts that affect the amount of charge 524 adjacent to the conductive element 520. If such byproducts are produced in small amounts or rapidly decay or react with other constituents, multiple copies of the same analyte may be analyzed in the reaction region 380 at the same time in order to increase the individual output signals generated by the group of chemical sensors 331.1-331.4. In an embodiment, multiple copies of an analyte may be attached to a solid phase support 512, either before or after deposition into the reaction region 380. The solid phase support 512 may be microparticles, nanoparticles, beads, solid or porous gels, or the like. For simplicity and ease of explanation, solid phase support 512 is also referred herein as a particle. For a nucleic acid analyte, multiple, connected copies may be made by rolling circle amplification (RCA), exponential RCA, Recombinase Polymerase Amplification (RPA), Polymerase Chain Reaction amplification (PCR), emulsion PCR amplification, or like techniques, to produce an amplicon without the need of a solid support.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals from the chemical sensors indicative of ion concentration during each nucleotide flow, the identity of the type, sequence and number of nucleotide(s) associated with a sample nucleic acid present in a reaction region coupled to a group of chemical sensors can be determined.

FIGS. 6 to 10 illustrate stages in a manufacturing process for forming a device including multiple chemical sensors coupled to the same reaction region according to a first embodiment.

Figure 6:
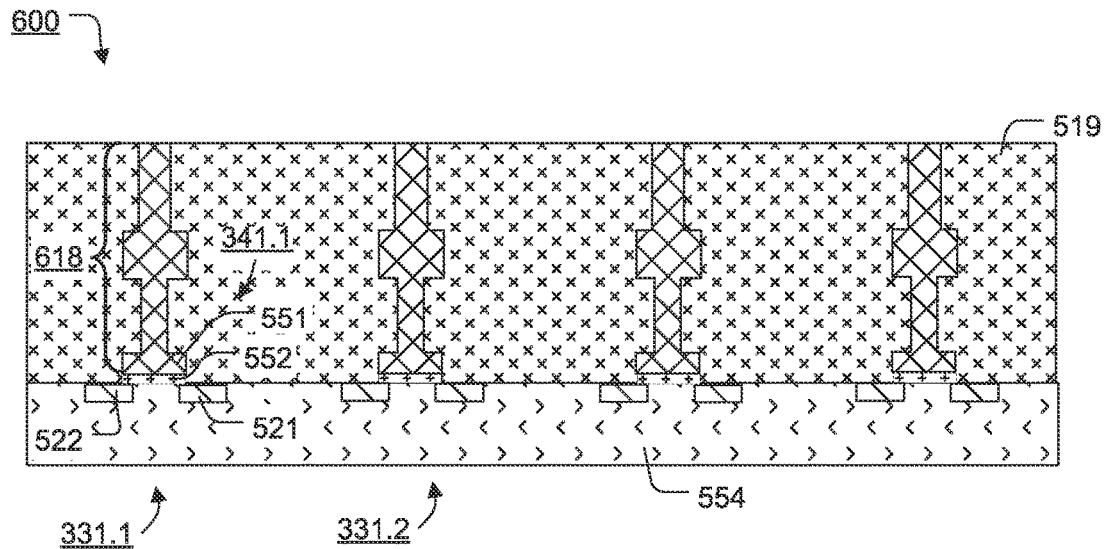
FIGS. 6 to 10 illustrate stages in a manufacturing process for forming a device including multiple chemical sensors coupled to the same reaction region according to a first embodiment.

FIG. 6 illustrates a structure 600 formed in a first stage. The structure 600 includes partially completed floating gate structures for the field effect transistors of the chemical sensors. For example, the structure 600 includes partially completed floating gate structure 618 for the chemically-sensitive field effect transistor 341.1 of the chemical sensor 331.1.

The structure 600 can be formed by depositing a layer of gate dielectric material on the semiconductor substrate 554, and depositing a layer of polysilicon (or other electrically conductive material) on the layer of gate dielectric material. The layer of polysilicon and the layer gate dielectric material can then be etched using an etch mask to form the gate dielectric elements (e.g. gate dielectric 552) and the lowermost conductive material element (e.g. conductive element 551) of the floating gate structures. Following formation of an ion-implantation mask, ion implantation can then be performed to form the source and drain regions (e.g. source region 52 land a drain region 522) of the chemical sensors.

A first layer of the dielectric material 519 can then be deposited over the lowermost conductive material elements. Conductive plugs can then be formed within vias etched in the first layer of dielectric material 519 to contact the lowermost conductive material elements of the floating gate structures. A layer of conductive material can then be deposited on the first layer of the dielectric material 519 and patterned to form second conductive material elements electrically connected to the conductive plugs. This process can then be repeated multiple times to form the partially completed floating gate structures shown in FIG. 6. Alternatively, other and/or additional techniques may be performed to form the structure.

Forming the structure 600 in FIG. 6 can also include forming additional elements such as array lines (e.g. row lines, column lines, etc.) for accessing the chemical sensors, additional doped regions in the substrate 554, and other circuitry (e.g. select switches, access circuitry, bias circuitry etc.) used to operate the chemical sensors, depending upon the device and array configuration in which the chemical sensors are implemented.

Next, conductive material 700 is formed on the structure illustrated in FIG. 6 to contact the partially completed floating gate structures. An etch mask including mask elements 720, 722 is then formed on the conductive material 700, resulting in the structure illustrated in FIG. 7.

The conductive material 700 includes one or more layers of electrically conductive material. For example, the conductive material 700 may include a layer of titanium nitride formed on a layer of aluminum, or a layer of titanium nitride formed on a layer of copper. Alternatively, the number of layers may be different than two, and other and/or additional conductive materials may be used. Examples of conductive materials that can be used in some embodiments include tantalum, aluminum, lanthanum, titanium, zirconium, hafnium, tungsten, palladium, iridium, etc., and combinations thereof.

The locations of the mask elements 720, 722 define the locations of the sensor plates for the chemically-sensitive field effect transistors of the corresponding groups of chemical sensors. In the illustrated embodiment, the mask elements 720, 722 comprise photoresist material which has been patterned using a lithographic process. Alternatively, other techniques and materials may be used.

Figure 8:
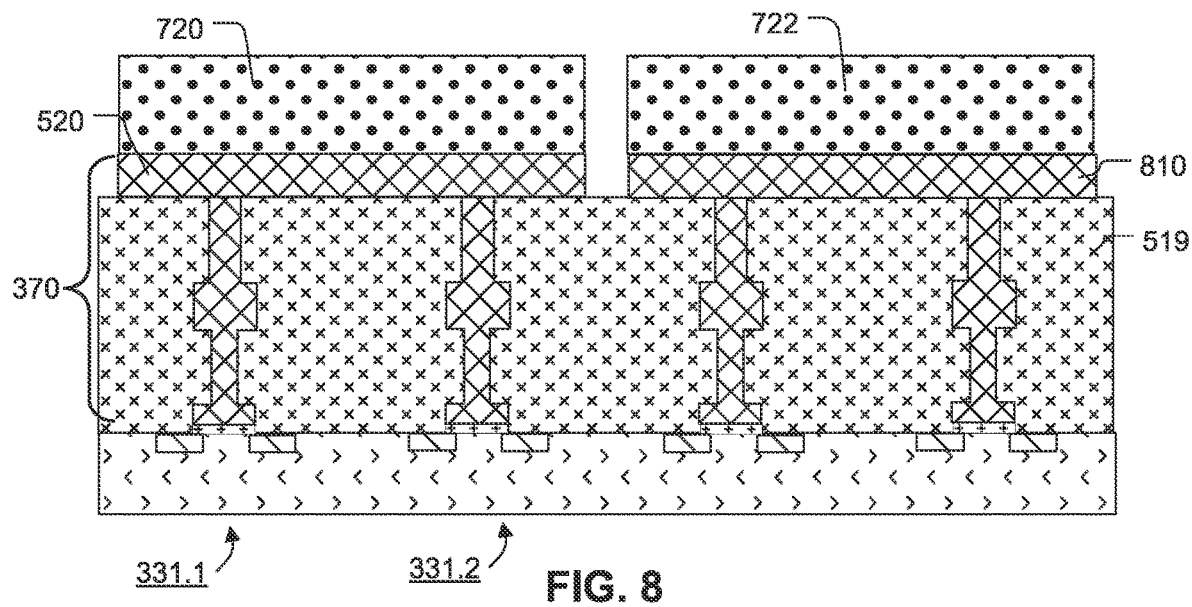

Next, the conductive material 700 is etched using the mask elements 700, 722 as a mask, resulting in the structure illustrated in FIG. 8. The etching process forms conductive elements 520, 810 in electrical contact with the partially completed floating gate structures of a corresponding group of sensors. The conductive element 520 electrically connects the partially completed floating gate structures for a group of sensors 331.1-331.4, to complete the common floating gate 370 for this group of sensors. Similarly, the conductive material element 810 completes the common floating gate for the adjacent group of sensors.

Figure 9:
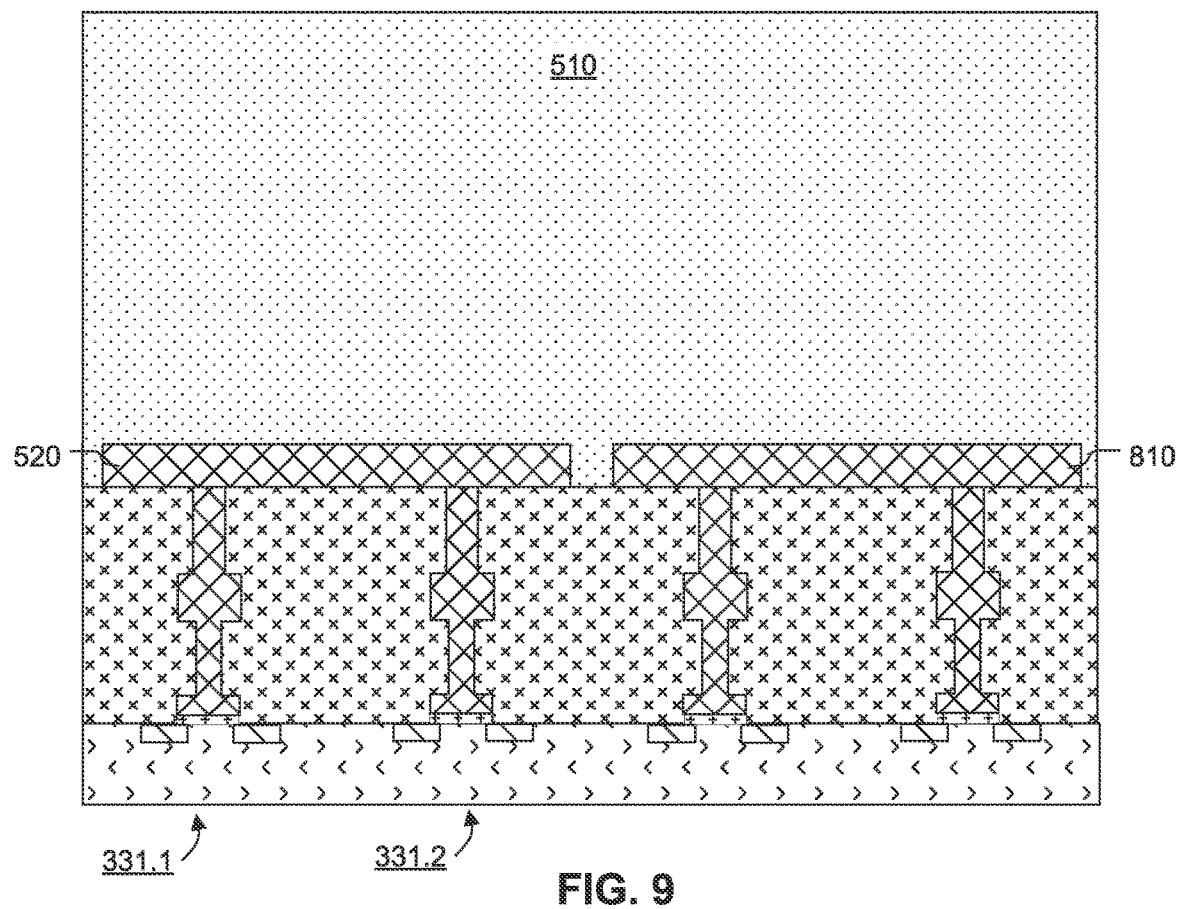

Next, the mask elements 700, 722 are removed and dielectric material 510 is formed, resulting in the structure illustrated in FIG. 9. The dielectric material 510 may comprise one or more layers of deposited dielectric material, such as silicon dioxide or silicon nitride.

Figure 10:
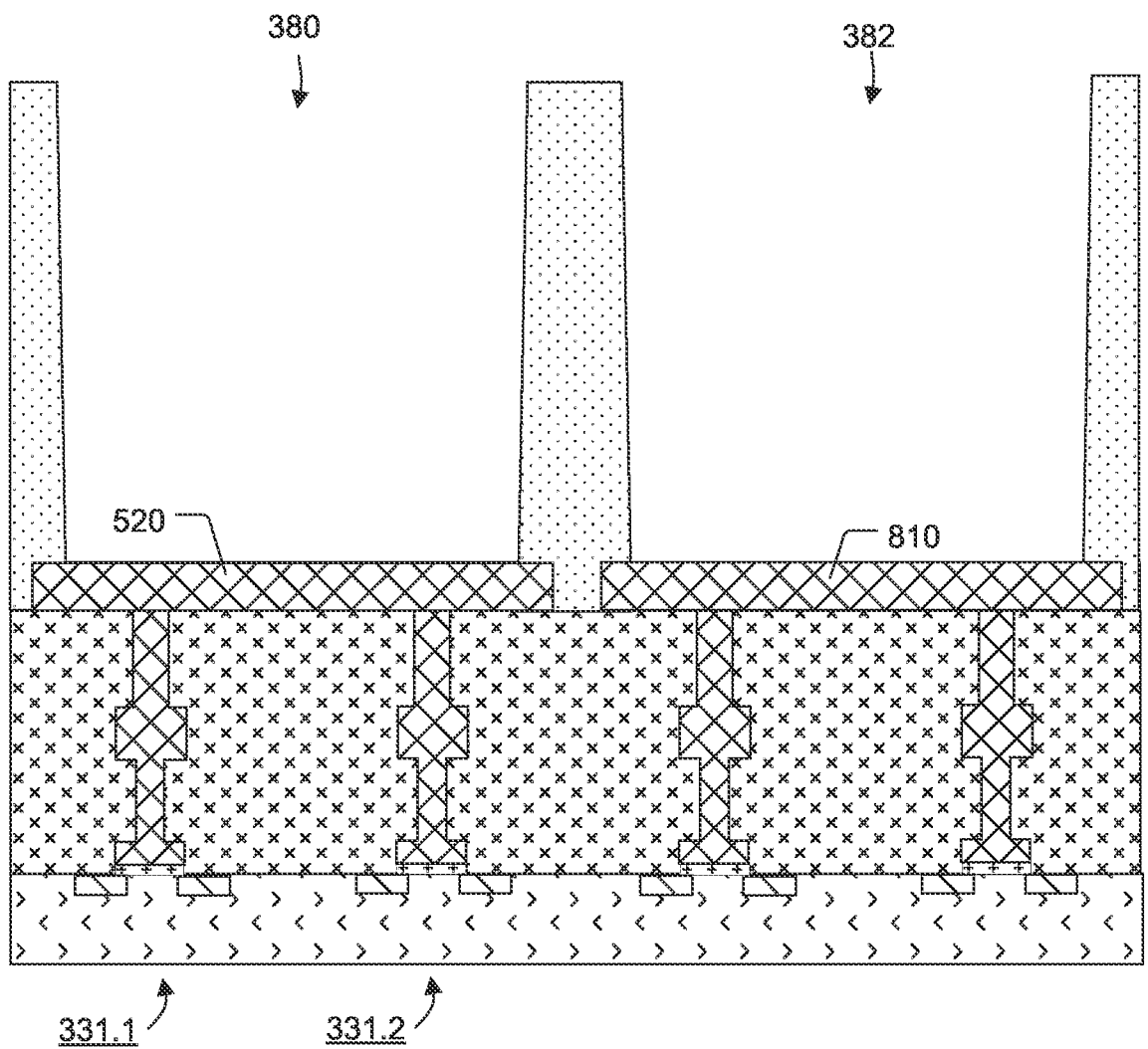

Next, the dielectric material 510 is etched to form openings defining reaction regions 380, 382 extending to upper surfaces of the conductive material elements 520, 810, resulting in the structure illustrated in FIG. 10.

Figure 11:
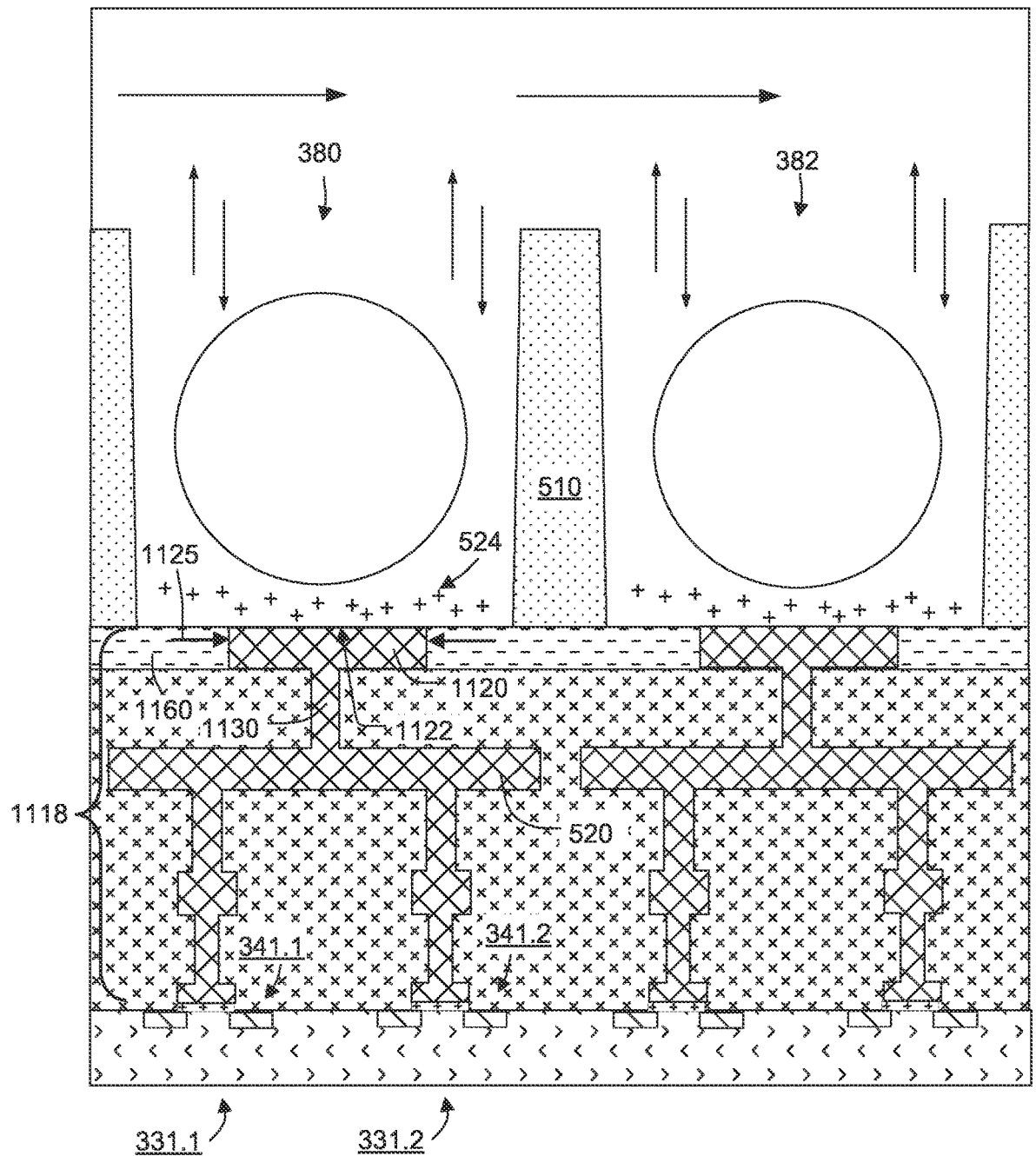
FIG. 11 illustrates a cross-sectional view of portions of two groups of chemical sensors and their corresponding reaction regions according to a second embodiment.

FIG. 11 illustrates a cross-sectional view of portions of two groups of chemical sensors and their corresponding reaction regions according to a second embodiment. In contrast to the embodiment shown in FIG. 5, the common floating gate for each group of chemical sensors includes a sensor plate that is smaller than the bottom surface of the corresponding reaction region.

In FIG. 11, the floating gate structure 1118 for the group of chemical sensors 331.1-331.4 includes conductive element 1120 coupled to the reaction region 380. The conductive element 1120 is coupled to the conductive element 520 by conductive plug 1130. The conductive element 1120 is the uppermost floating gate conductor in the floating gate structure 1118, and thus acts as the sensor plate for the group of chemical sensors 331.1-331.4.

In FIG. 11, an upper surface 1122 of the conductive element 1120 is a portion of the bottom surface of the reaction region 380. That is, there is no intervening deposited material layer between the upper surface 1122 of the conductive element 1120 and the reaction region 380. As a result of this structure, the upper surface 1122 of the conductive element 1120 acts as the sensing surface for the group of chemical sensors 331.1-331.4. In the illustrated embodiment, the conductive element 1120 is within the dielectric material 1160, such that the upper surface 1122 of the conductive element 1120 is co-planar with the upper surface of the dielectric material 1160. Alternatively, the conductive element 1120 may be formed on the upper surface of dielectric material 1160, and thus protrude slightly into the reaction region 380.

As shown in FIG. 11, the upper surface 1122 of the conductive element 1120 has a width 1125 that is the less than the width of the bottom surface of the reaction region 380. As described in more detail below, having a small conductive element 1120 as the sensor plate can enable the signal-to-noise ratio (SNR) of the individual output signals of the chemical sensors 331.1-331.4 to be maximized.

The amplitude of the desired signal detected by the chemical sensors 331.1-331.4 in response to the charge 524 in an analyte solution is a superposition of the charge concentration along the interface between the conductive element 1120 and the analyte solution. Because the charge 524 is more highly concentrated at the bottom and middle of the reaction region 380, the width 1125 of the conductive element 1120 is a tradeoff between the amplitude of the desired signal detected in response to the charge 524, and the fluidic noise due to random fluctuation between the conductive element 1120 and the analyte solution. Increasing the width 1125 of the conductive element 1120 increases the fluidic interface area for the chemical sensors 331.1-331.4, which reduces fluidic noise. However, since the localized surface density of charge 524 decreases with distance from the middle of the reaction region 380, the conductive element 1120 detects a greater proportion of the signal from areas having lower charge concentration, which can reduce the overall amplitude of the detected signal. In contrast, decreasing the width 1122 of the conductive element 1120 reduces the sensing surface area and thus increases the fluidic noise, but also increases the overall amplitude of the detected signal.

For a very small sensing surface area, Applicants have found that the fluidic noise changes as a function of the sensing surface area differently than the amplitude of the desired signal. Because the SNR of an individual output signal is the ratio of these two quantities, there is an optimal width 1125 at which the SNR of the individual output signals from the chemical sensors 331.1-331.2 is maximum.

The optimal width 1125 can vary from embodiment to embodiment depending on the material characteristics of the conductive element 1120 and the dielectric materials 510, 1160, the volume, shape, aspect ratio (such as base width-to-well depth ratio), and other dimensional characteristics of the reaction regions, the nature of the reaction taking place, as well as the reagents, byproducts, or labeling techniques (if any) that are employed. The optimal width may for example be determined empirically.

Figure 12:
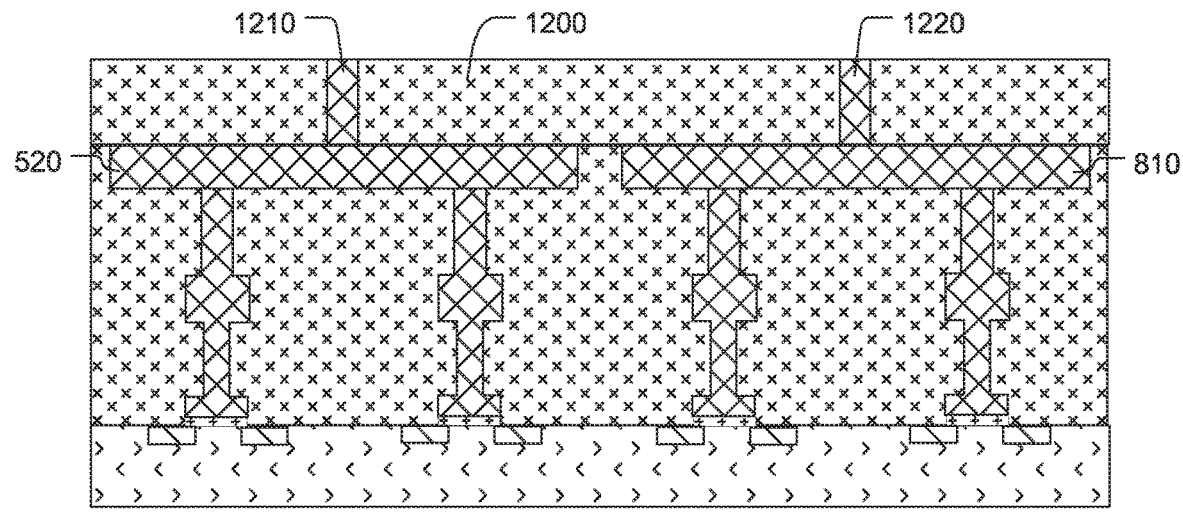
FIGS. 12 to 14 illustrate stages in a manufacturing process for forming a device including multiple chemical sensors coupled to the same reaction region according to a second embodiment.
Figure 13:
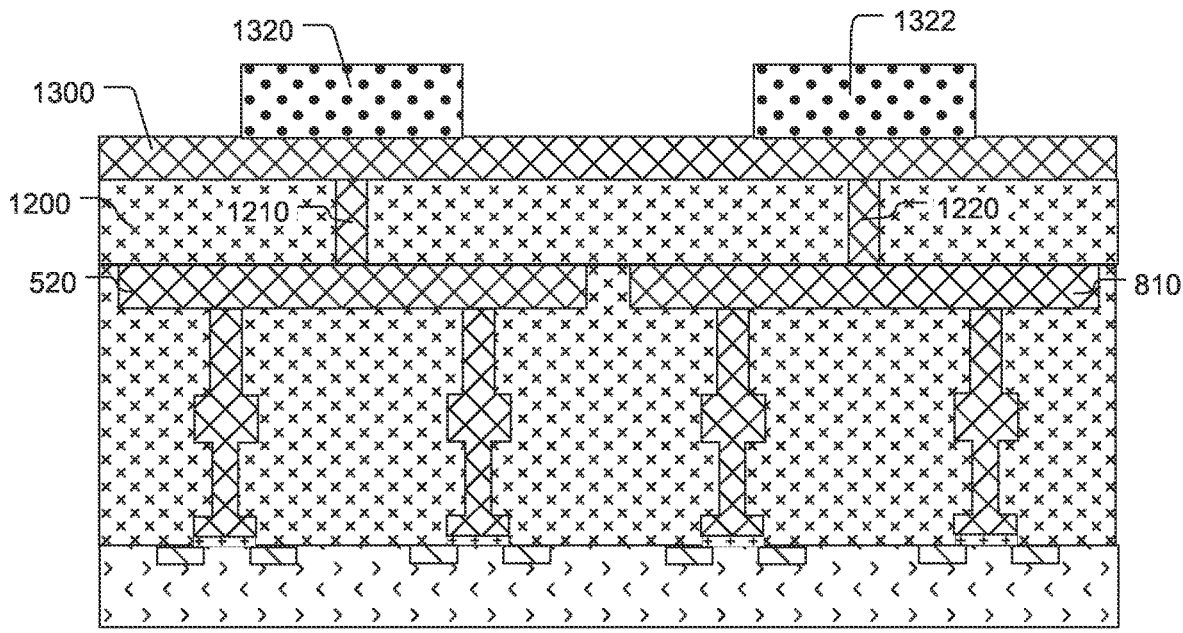
Figure 14:
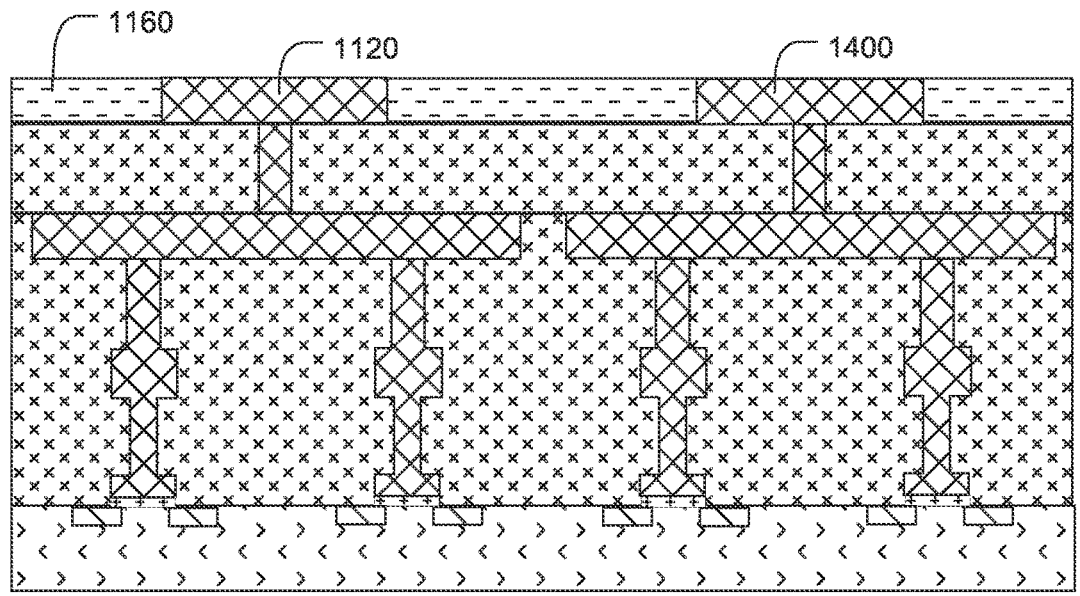

FIGS. 12 to 14 illustrate stages in a manufacturing process for forming a device including multiple chemical sensors coupled to the same reaction region according to a second embodiment.

FIG. 12 illustrates a first stage of forming conductive plugs 1210, 1220 extending through dielectric material 1200 to contact the conductive elements 520, 810 of the structure illustrated in FIG. 8. The structure in FIG. 12 can be formed by removing the mask elements 720, 722 in FIG. 8 and forming dielectric material 1200 on the resulting structure. Vias can then be etched through the dielectric material 1200, and metal deposited within the vias. A planarization process (e.g. chemical mechanical polishing) can then be performed to remove the deposited metal from the upper surface of the dielectric material 1200 and form the plugs 1210, 1220. Alternatively, other techniques may be used.

Next, conductive material 1300 is formed on the structure illustrated in FIG. 12. An etch mask including mask elements 1320, 1322 is then formed on the conductive material 1300, resulting in the structure illustrated in FIG. 13.

Figure 7:
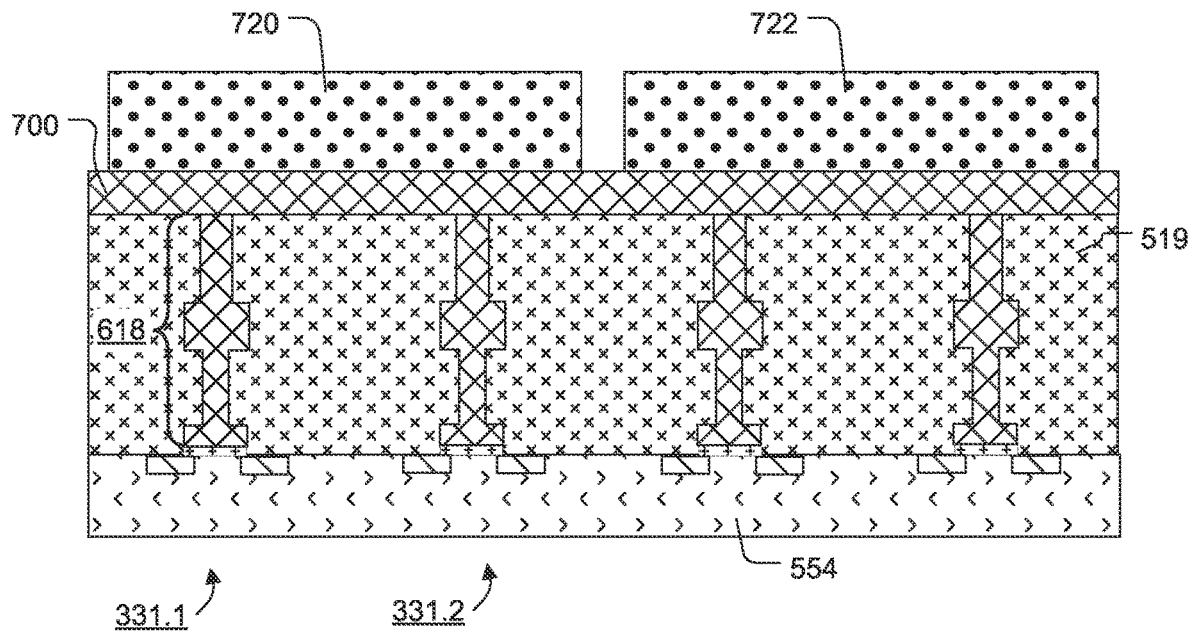

The conductive material 1300 may comprise one or more layers of conductive material, such as those described above with respect the conductive material 700 of FIG. 7. The locations of the mask elements 1320, 1322 define the locations of the sensor plates of the field effect transistors of the corresponding groups of chemical sensors. In the illustrated embodiment, the mask elements 1320, 1322 comprise photoresist material which has been patterned using a lithographic process. Alternatively, other techniques and materials may be used.

Next, the conductive material 1300 is etched using the mask elements 1320, 1322 as a mask to form the conductive elements 1120, 1400. Dielectric material 1160 is then formed between the conductive elements 1120, 1400, resulting in the structure illustrated in FIG. 14.

Next, dielectric material 510 is formed on the structure illustrated in FIG. 14. The dielectric material 510 is then be etched to form openings defining reaction regions 380, 382 extending to upper surfaces of the conductive elements 1120, 1400, resulting in the structure illustrated in FIG. 11. The dielectric material 1160 may comprise material different than that of dielectric material 510. For example, the dielectric material 510 may comprise material (e.g. silicon oxide) which can be selectively etched relative to the material (e.g. silicon nitride) of the dielectric material 1160 when subjected to a chosen etch process. In such a case, the dielectric material 1160 can act as an etch stop during the etching process used to form the reaction regions 380, 382. In doing so, the dielectric material 1160 can prevent etching past the conductive elements 1120, 1400, and thus can define and maintain the desired shape of the reaction regions 380, 382.

FIGS. 15 to 18 illustrate stages in a manufacturing process for forming a device including multiple chemical sensors coupled to the same reaction region according to a third embodiment.

Figure 15:
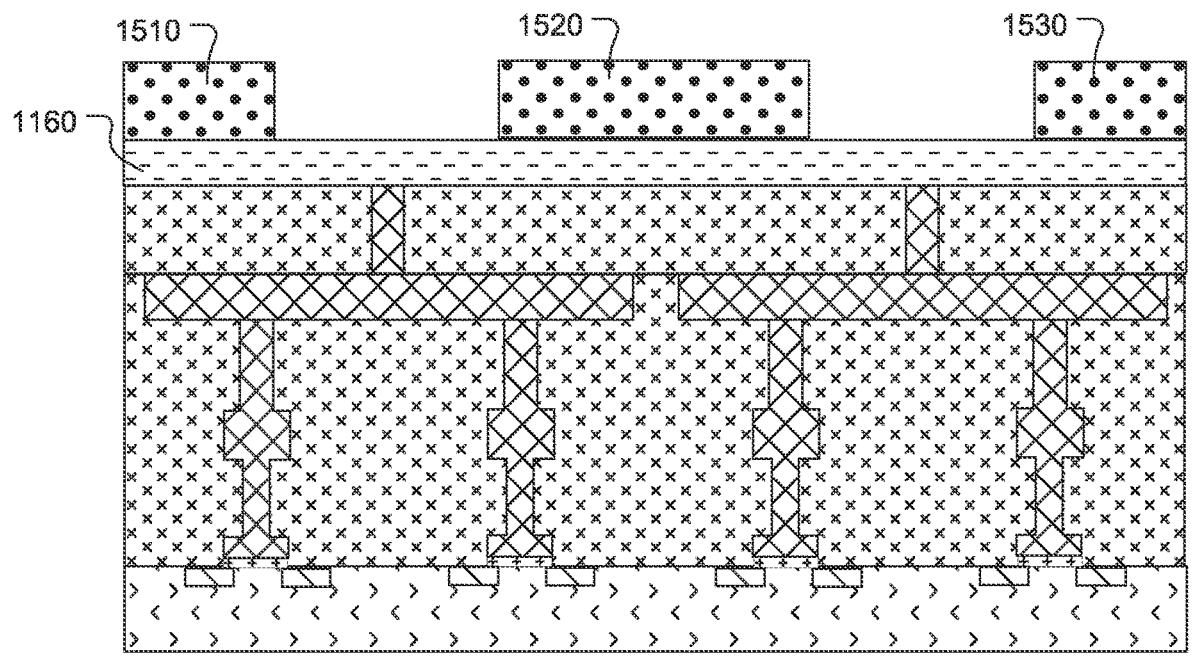
FIGS. 15 to 18 illustrate stages in a manufacturing process for forming a device including multiple chemical sensors coupled to the same reaction region according to a third embodiment.

FIG. 15 illustrates a first stage of forming dielectric material 1160 on the structure illustrated in FIG. 12. An etch mask including mask elements 1510, 1520, 1530 is then formed on the dielectric material 1160, resulting in the structure illustrated in FIG. 15. As described in more detail below, openings between the mask elements 1510, 1520, 1530 define the locations of the sensor plates of the field effect transistors of the corresponding groups of chemical sensors.

Figure 16:
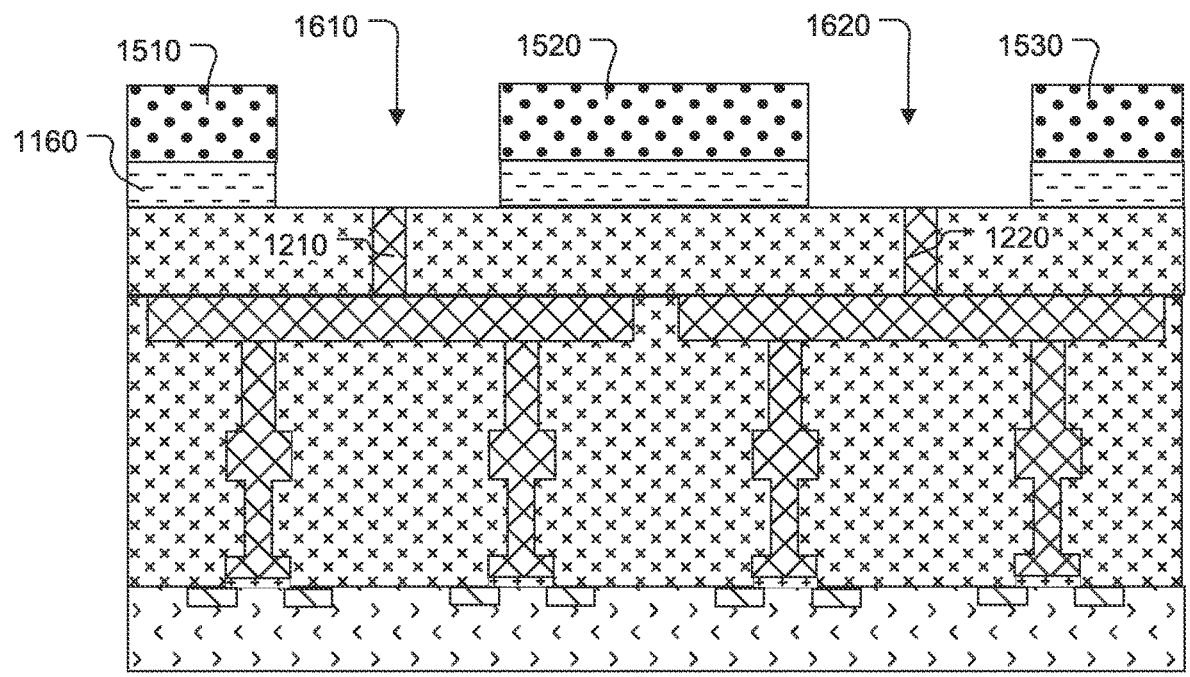

Next, the dielectric material 1160 is etched using the mask elements 1510, 1520, 1530 as an etch mask to form openings 1610, 1620 within the dielectric material 1160, resulting in the structure illustrated in FIG. 16. As shown in FIG. 16, the openings extend to the upper surfaces of the conductive plugs 1210, 1220.

Figure 17:
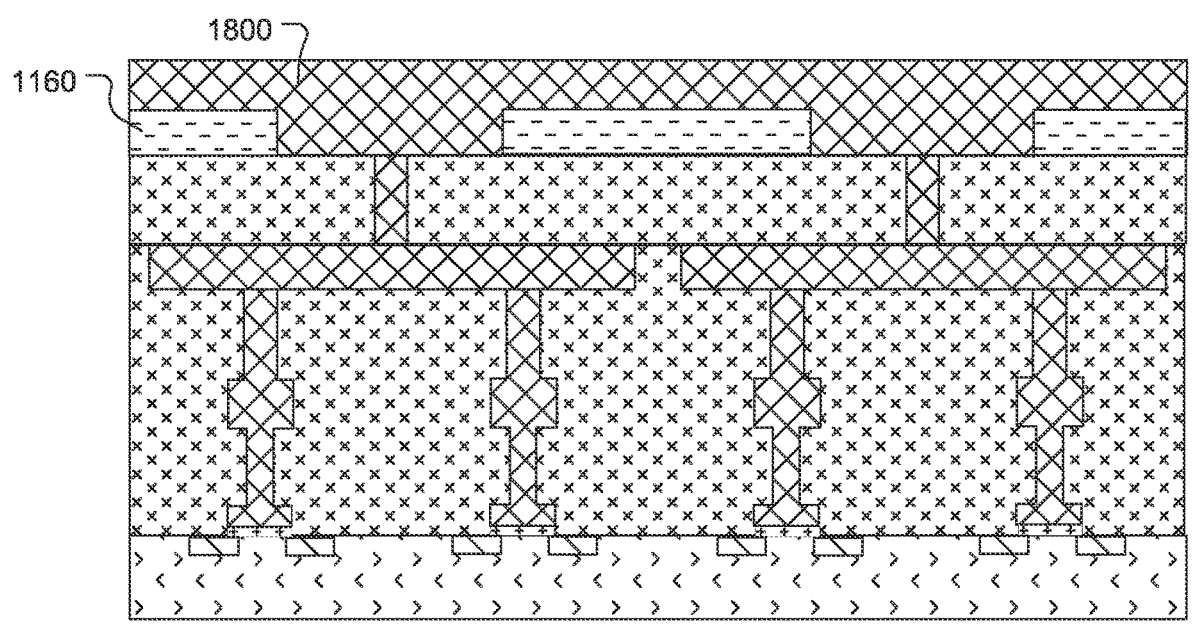

Next, the mask elements 1510, 1520, 1530 are removed and conductive material 1800 is deposited on the structure illustrated in FIG. 16, resulting in the structure illustrated in FIG. 17. The conductive material 1800 may comprise one or more layers of conductive material, such as those described above with respect the conductive material 700 of FIG. 7.

Figure 18:
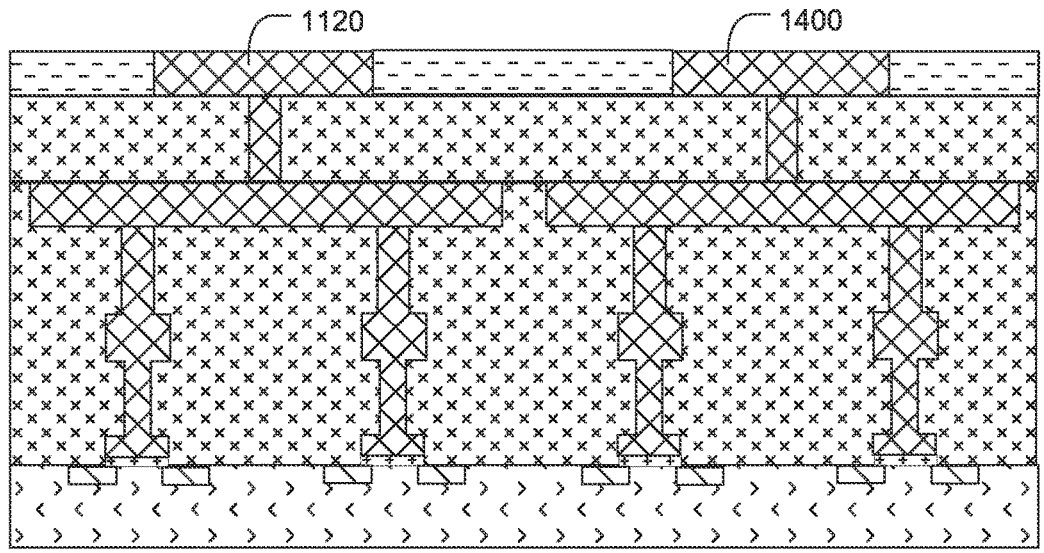

Next, a planarization process (e.g. CMP) is performed to remove the conductive material 1800 from the upper surface of the dielectric material 1160, resulting in the structure illustrated in FIG. 18. The planarization process leaves remaining conductive material within the openings 1610, 1620 to form the conductive elements 1120, 1400.

Next, dielectric material 510 is formed on the structure illustrated in FIG. 18. The dielectric material 510 can then be etched to form openings defining reaction regions 380, 382 extending to upper surfaces of the conductive elements 1120, 1400, resulting in the structure illustrated in FIG. 11.

Figure 19:
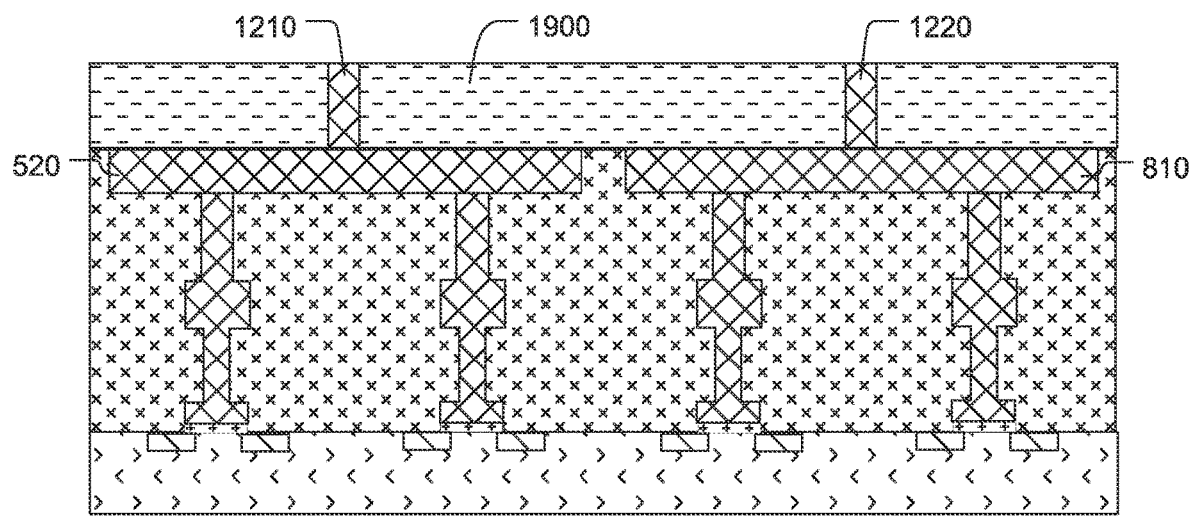
FIGS. 19 to 21 illustrate stages in a manufacturing process for forming a device including multiple chemical sensors coupled to the same reaction region according to a fourth embodiment.
Figure 20:
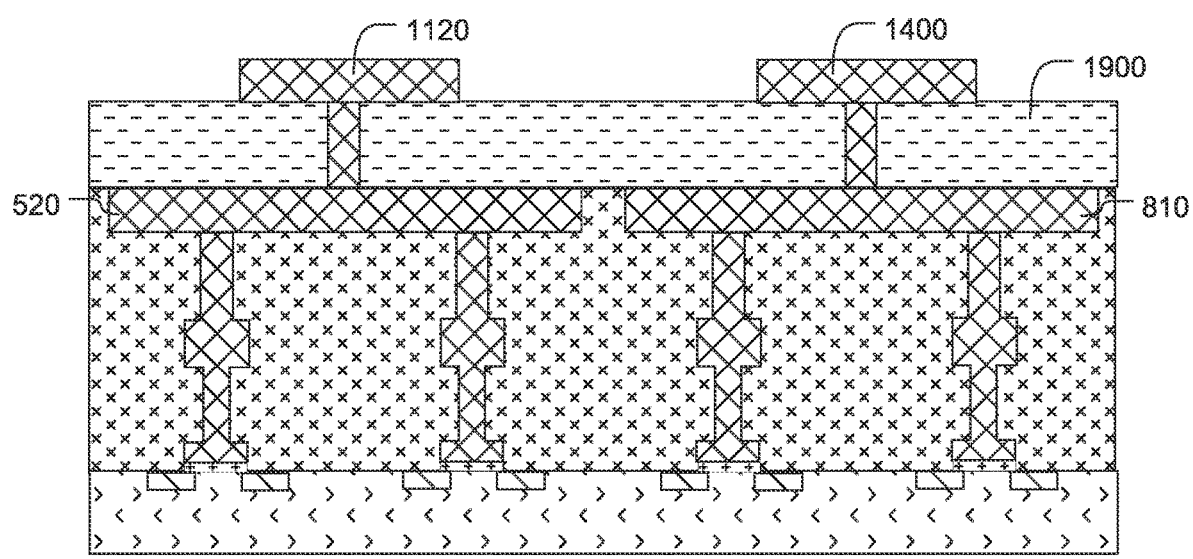
Figure 21:
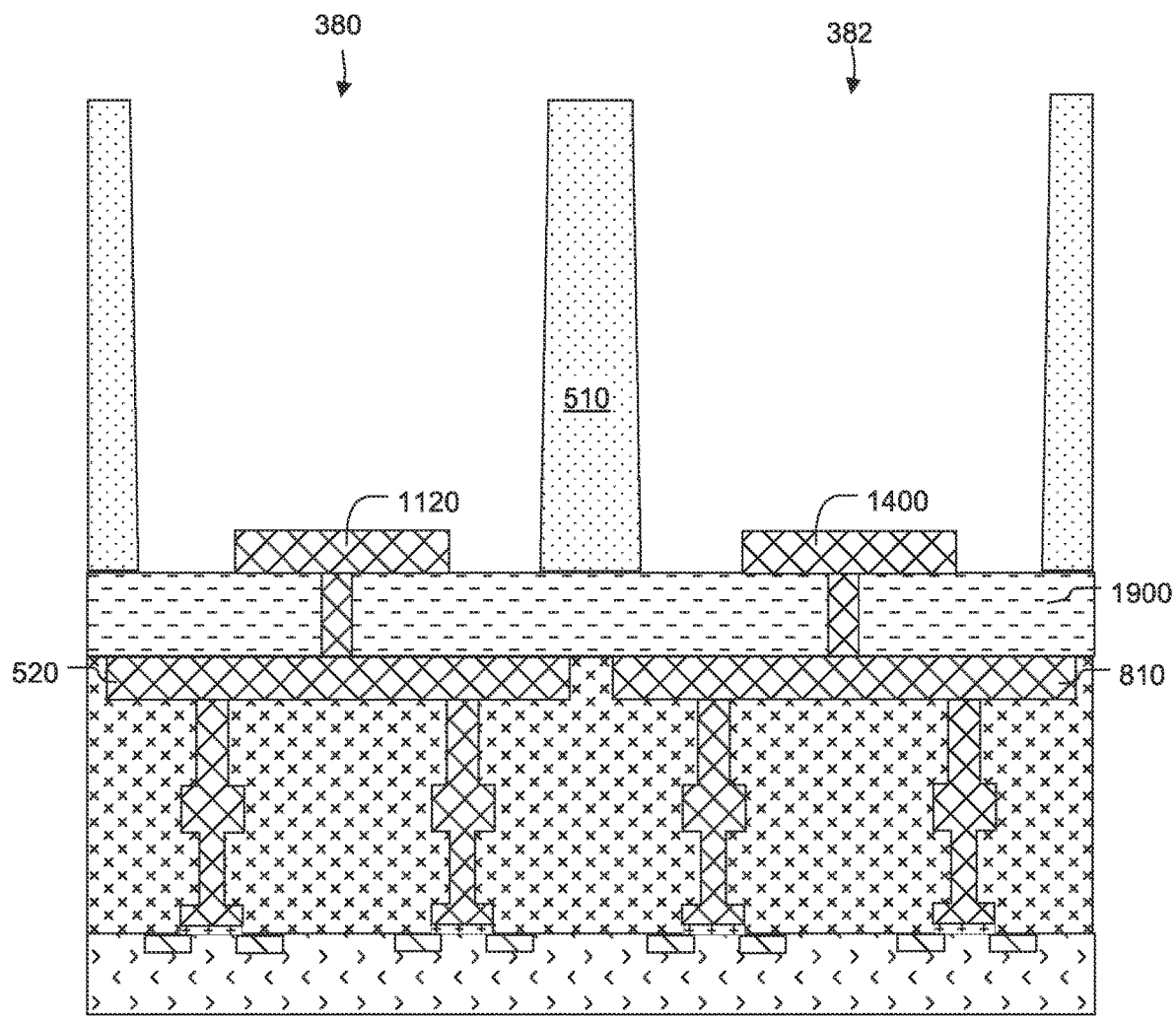

FIGS. 19 to 21 illustrate stages in a manufacturing process for forming a device including multiple chemical sensors coupled to the same reaction region according to a fourth embodiment.

FIG. 19 illustrates a first stage of forming conductive plugs 1210, 1220 extending through dielectric material 1900 to contact the conductive elements 520, 810 of the structure illustrated in FIG. 8. As described in more detail below, the dielectric material 1900, comprising one or more layers of dielectric material, acts an etch stop during the subsequent formation of the reaction regions 380, 382. The structure in FIG. 19 can be formed by removing the mask elements 720, 722 illustrated in FIG. 8 and forming the dielectric material 1900 on the resulting structure. The plugs 1210, 1220 can then be formed using the techniques described above with reference to FIG. 12. Alternatively, other techniques may be used.

Next, conductive elements 1120, 1400 are formed on the upper surface of the dielectric material 1900, resulting in the structure illustrated in FIG. 20. The conductive elements 1120, 1400 may be formed by depositing conductive material, forming an etch mask including mask elements defining the locations of the conductive elements 1120, 1400, and etching the conductive material using the mask elements as an etch mask.

Next, dielectric material 510 is formed on the structure illustrated in FIG. 20. The dielectric material 510 is then be etched to form openings defining reaction regions 380, 382 extending to upper surfaces of the conductive elements 1120, 1400, resulting in the structure illustrated in FIG. 21. As shown in FIG. 21, in this embodiment the reaction regions 380, 382 extend below the upper surfaces of the conductive elements 1120, 1400 to expose their side surfaces.

The dielectric material 1900 may comprise material different than that of dielectric material 510. For example, the dielectric material 510 may comprise material (e.g. silicon oxide) which can be selectively etched relative to the material (e.g. silicon nitride) of the dielectric material 1900 when subjected to a chosen etch process. In such a case, the dielectric material 1900 can act as an etch stop during the etching process used to form the reaction regions 380, 382. In doing so, the dielectric material 1900 can prevent etching below the conductive elements 1120, 1400, and thus can define and maintain the shape of the reaction regions 380, 382.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed:

1. An apparatus, comprising:
    a chemically-sensitive field effect transistor (chemFET) sensor device comprising:
        an array of reaction regions;
        at least two chemFET sensors coupled to each reaction region of the array of reaction regions, wherein each chemFET sensor of the at least two chemFET sensors comprises a chemFET and a row select transistor; and
        a floating gate common to the at least two chemFET sensors and in communication with each respective reaction region;
    a row select circuit for biasing each row select transistor of each chemFET sensor of the at least two chemFET sensors for each reaction region in the array of reaction regions;
    a column output circuit for coupling each chemFET of the at the least two chemFET sensors for each reaction region in the array of reaction regions to a respective column line in response to biasing each respective row select transistor; and
    an array controller comprising memory for storage of data and software applications, and a processor for accessing data and executing applications.

2. The apparatus of claim 1, wherein the array controller is configured to:
    acquire an individual output signal from each chemFET sensor of the at least two chemFET sensors for each reaction region in the array of reaction regions; and
    calculate a resultant output signal for each at least two chemFET sensors for each reaction region in the array of reaction regions based on one or more of the individual output signals.

3. The apparatus of claim 1, further comprising a fluidics system including:
    a valve block for controllable fluid communication between a plurality of reagents and a flow cell housing the chemFET sensor device; and
    a reference electrode placed in fluid communication with the chemFET sensor device.

4. The apparatus of claim 3, wherein the array controller provides a reference bias voltage to the reference electrode.

5. The apparatus of claim 1, wherein the chemFET sensor device is an ion-sensitive field effect transistor (ISFET) sensor device.

6. The apparatus of claim 5, wherein the ISFET sensor device is sensitive to hydrogen.

7. The apparatus of claim 1, wherein an upper surface of a conductive element of each floating gate common to the at least two chemFET sensors for each reaction region of the array of reaction regions comprises a sensing surface including one or more conductive elements.

8. The apparatus of claim 7, wherein the conductive element of each floating gate comprises a metal or a ceramic.

9. The apparatus of claim 8, wherein the metal comprises at least one of aluminum, copper, nickel, titanium, silver, gold, platinum, hafnium, lanthanum, tantalum, tungsten, iridium, zirconium, or palladium.

10. The apparatus of claim 8, wherein the ceramic comprises at least one of titanium nitride, titanium aluminum nitride, titanium oxide, or tantalum nitride.

11. The apparatus of claim 7, wherein the conductive element of the sensing surface comprises titanium nitride, titanium oxide, or titanium oxynitride.

12. The apparatus of claim 7, wherein the sensing surface is sensitive to ions.

13. The apparatus of claim 12, wherein the sensing surface is sensitive to hydrogen.

14. A method for sequencing comprising:

sequentially flowing a series of deoxynucleoside triphosphate (dNTP) solutions over an array of reaction regions, each reaction region coupled to at least two chemFET sensors having a common floating gate in communication with a respective reaction region;

coupling column output circuitry to each chemFET of each respective at least two chemFET sensors of each reaction region of the array of reaction regions in response to biasing each respective row select transistor coupled to each chemFET of each respective at least two chemFET sensors;

acquiring an individual output signal for each chemFET of the at least two chemFET sensors for each reaction region in the array of reaction regions in response to release of an analyte resulting from incorporation of a nucleotide to a template nucleic acid in a reaction region of the array of reaction regions; and calculating a resultant output signal for each at least two chemFET sensors for each reaction region in the array of reaction regions based on one or more of the individual output signals.

15. The method of claim 14, wherein the method further comprises:

determining a sequence corresponding for each reaction region in the array of reaction regions loaded with a template nucleic acid-containing bead based on the resultant output signal for each at least two chemFET sensors for each reaction region in the array of reaction regions.

16. The method of claim 14, wherein an upper surface of each floating gate common to the at least two chemFET sensors for each reaction region of the array of reaction regions comprises a sensing surface including one or more conductive elements.

17. The method of claim 16, wherein the sensing surface is sensitive to ions.

18. The method of claim 17, wherein the sensing surface is sensitive to hydrogen.

19. The method of claim 14, wherein the at least two chemFET sensors for each reaction region in the array of reaction regions are ion-sensitive field effect (ISFET) sensors.

20. The apparatus of claim 7, wherein the sensing surface is additionally formed on a sidewall of each corresponding reaction region of the array of reaction regions.

* * * * *